United States Patent [19]

Bugaut et al.

[11] Patent Number: 4,863,480

[45] Date of Patent: Sep. 5, 1989

[54] SUBSTITUTED METAAMINOPHENOLS, A PROCESS FOR THEIR PREPARATION, HAIR DYEING COMPOSITIONS CONTAINING THEM AND A HAIR-DYEING PROCESS

[75] Inventors: Andrée Bugaut, Boulogne; Alex Junino, Aulnay, both of France

[73] Assignee: The French joint stock company "L'Oreal", Paris, France

[21] Appl. No.: 618,149

[22] Filed: Jun. 7, 1984

[30] Foreign Application Priority Data

Jun. 13, 1983 [FR] France ................. 83 09734

[51] Int. Cl.$^4$ .................... A61K 7/13; C07C 91/40
[52] U.S. Cl. ................................. 8/408; 8/409; 8/410; 8/412; 8/421; 564/443
[58] Field of Search ................... 564/443; 8/421

[56] References Cited

U.S. PATENT DOCUMENTS 3,834,866  9/1974  Pum ..................... 564/443

FOREIGN PATENT DOCUMENTS

| 0029964 | 11/1980 | European Pat. Off. |
| 3145811 | 5/1983 | Fed. Rep. of Germany ...... 564/443 |
| 1295341 | 5/1962 | France . |
| 2456726 | 12/1980 | France . |
| 2516507 | 5/1983 | France . |
| 303097 | 12/1928 | United Kingdom . |
| 2078747 | 1/1982 | United Kingdom . |
| 2111490 | 7/1983 | United Kingdom ............. 564/443 |

*Primary Examiner*—Glennon H. Hollrah
*Assistant Examiner*—Peter G. O'Sulllivan
*Attorney, Agent, or Firm*—Cushman, Darby & Cushman

[57] ABSTRACT

A new substituted metaaminophenol of formula (I):

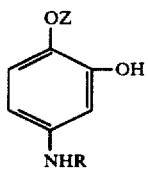

(I)

wherein Z represents a monohydroxylated or polyhydroxylated hydrocarbon radical of 1 to 6 carbon atoms or an aminoalkyl radical of the formula:

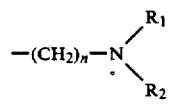

wherein n is an integer from 1 to 6 and $R_1$ and $R_2$, which are identical or different, represent a hydrogen atom or an alkyl or hydroxyalkyl radical of 1 to 6 carbom atoms or an acyl radical of 1 to 4 carbon atoms, and R represents a hydrogen atom, an alkyl radical or monohydroxyalkyl or polyhydroxyalkyl, monocarbamylalkyl, dicarbamylalkyl, aminoalkyl, acyl, carbalkoxy, carbamyl or monoalkylcarbamyl radical, the abovementioned alkyl radicals containing 1 to 6 carbon atoms, or an acid salt thereof with the proviso that if R represents a hydrogen atom, Z cannot represent —$CH_2CH_2OH$ is disclosed, together with a process for their preparation, hair-dyeing compositions containing them and a hair-dyeing process.

20 Claims, 4 Drawing Sheets

SUBSTITUTED METAAMINOPHENOLS, A PROCESS FOR THEIR PREPARATION, HAIR DYEING COMPOSITIONS CONTAINING THEM AND A HAIR-DYEING PROCESS

The present invention relates to new substituted metaaminophenols. These compounds can be used as couplers for oxidation hair dyeing, in the presence of oxidation bases.

The invention also relates to a hair-dyeing process using compositions containing the metaaminophenols and a process for the preparation of the new chemical compounds.

One object of the invention is to provide new chemical compounds which can be used as couplers in hair dyes to give strong colourations which are stable to light, have a good resistance to weather and washing, provide compounds which can have a good degree of harmlessness and satisfactory characteristics from the point of view of mutagenesis and which lead, by means of an oxidative reaction with oxidation bases in an alkaline medium, to non-mutagenic indoaniline or indophenol derivatives.

The present invention provides a metaaminophenol of formula (I):

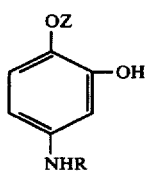

(I)

wherein Z represents a monohydroxylated or polyhydroxylated hydrocarbon radical of 1 to 6 carbon atoms or an aminoalkyl radical of the formula:

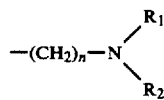

wherein n is an integer from 1 to 6 and $R_1$ and $R_2$, which are identical or different, represent a hydrogen atom or an alkyl or hydroxyalkyl radical of 1 to 6 carbon atoms or an acyl radical of 1 to 4 carbon atoms, and R represents a hydrogen atom, an alkyl radical or a monohydroxyalkyl or polyhydroxyalkyl, monocarbamylalkyl, dicarbamylalkyl, aminoalkyl, acyl, carbalkoxy, carbamyl or monoalkylcarbamyl radical, the abovementioned alkyl radicals containing 1 to 6 carbon atoms, and its acid salts, particularly the hydrochloride or sulphate, with the proviso that if R represents a hydrogen atom, Z cannot represent —$CH_2CH_2OH$.

Preferably Z represents —$CH_2CH_2OH$, —$CH_2$—$CHOH$—$CH_2OH$, —$CH_2$—$CHOH$—$CH_3$, —$CH_2$—$CH_2$—$NH_2$, —$CH_2$—$CH_2$—$NHCH_3$, —$CH_2$—$CH_2$—$NHCOCH_3$ or

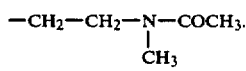

R is preferably a formyl, acetyl or propionyl group if it is an acyl radical or a hydrogen atom.

Chemical compounds similar to compounds of the present invention are described in French Pat. No. 1,543,690. However, these compounds are metaaminophenols in which the substituent in the ortho position to the phenol group is $OZ_1$, wherein $Z_1$ is a radical containing a hydroxyl group and an amine group at the end of the chain. In the compounds of the formula (I), the group Z is not derived from an alkanolamine but is either a monohydroxylated or polyhydroxylated radical or an alkylamine radical. This difference in structure results in considerable differences in the properties. Compounds described in French Pat. No. 1,543,690 β-adrenergic blocking activity (therapy of cardiac complaints), whereas compounds of the formula (I) are essentially of interest in the field of hair dyeing.

The process for the preparation of the compounds of the formula (I) as herein described is novel and has considerable practical advantages compared with the process of preparation described for the similar compounds in French Pat. No. 1,543,690. Furthermore, the process according to the invention also has a great advantage compared with the process described in U.S. Pat. No. 3,834,866 for metaaminophenols containing an $OCH_3$ substituent in the ortho position in which the process of manufacture described requires a nitration step at a temperature above 100° C., which results in the evolution of nitrous vapours and creates difficulties for manufacture on the industrial scale. The reaction of methanol with 3,4-methylenedioxy-1-nitrobenzene in the presence of potassium hydroxide is described in CHEM. PHARM. BULL., 3113–3116, 1978, Volume 26, but this reference does not describe nor suggest the reaction of the more complex alcohol Y—$CH_2OH$, in which Y has the meanings indicated earlier.

The compounds of formula (I) or their salts may be obtained by a process comprising in a first step, reacting 3,4-methylenedioxy-1-nitrobenzene, in the presence of a strong base such as potassium hydroxide, with an alcohol of the formula (II):

(II)

wherein Y represents either a monohydroxyalkyl or polyhydroxyalkyl group of 1 to 5 carbon atoms, or a group of the formula:

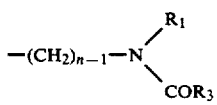

wherein $R_1$ and n have the meanings indicated above and $R_3$ represents a hydrogen atom or an alkyl radical of 1 to 3 carbon atoms and in a second step, the nitro group of the previously obtained compound of formula (III):

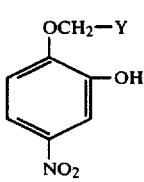

(III)

is reduced to give a compound of formula (IV):

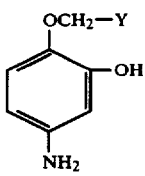

wherein Y has the meaning indicated above; and if appropriate, in a third step, according to the desired compound of the formula (I), the compound of formula (IV) is converted by acid hydrolysis, especially with hydrochloric acid if Y comprises an acylated amine group, or by substitution of the extranuclear amine if Y contains an amine group, or by monosubstitution of the aromatic amine.

The reduction of the nitro group of compounds of the formula (III) is preferably carried out using iron in an acetic acid medium or by using cyclohexene in the presence of a palladium/charcoal catalyst.

If the compound of the formula (IV) in which Y contains an acylated amine group, is subjected to hydrolysis with hydrochloric acid, a compound of the formula (V) is obtained:

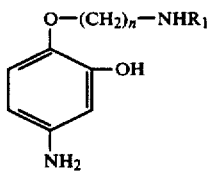

All the compounds of the formulae (IV) and (V), together with their derivatives obtained by substitution of the aromatic or extranuclear amine, cover all the compounds of formula (I). The aromatic or extranuclear amines may be substituted by reaction with, for example, ethyl bromide, glycol bromohydrin, ethyl chloroformate, β-chloroacetamide or acetic anhydride.

The present invention also provides a new oxidation dyeing composition for the hair, comprising at least one oxidation base, a cosmetic carrier, and at least one coupler of formula (I) and/or the corresponding acid salt.

In a preferred embodiment, the dyeing composition according to the invention comprises at least one oxidation base comprising (A) the paraphenylene diamines or paraaminophenols of formula (VI):

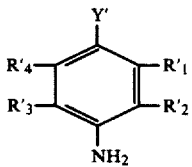

or acid salts of these compounds, wherein $R'_1$, $R'_2$, $R'_3$ and $R'_4$ independently of one another represent a hydrogen atom, a halogen atom or an alkyl, hydroxyalkyl, alkoxy or hydroxyalkoxy radical containing 1 to 4 carbon atoms, and Y' represents a hydroxyl group or an $NR'_5R'_6$ group, wherein $R'_5$ and $R'_6$ independently of one another are a hydrogen atom or an alkyl, monohydroxyalkyl or polyhydroxyalkyl, carbamylalkyl, mesylaminoalkyl or alkoxyalkyl radical of 1 to 4 carbon atoms; or (B) Heterocyclic oxidation bases and the corresponding acid salts, in particular 2,5-diaminopyridine.

Examples of oxidation bases of the formula (VI) are: paraphenylenediamine, paratoluylenediamine, chloroparaphenylenediamine, 2,6-dimethylparaphenylenediamine, N-β-hydroxyethylparaphenylenediamine, N-carbamylmethylparaphenylenediamine, 2,5-diaminophenoxyethanol, N,N-di-β-hydroxyethylparaphenylenediamine, N-carbamylmethyl-N-ethylparaphenylenediamine, N-methoxyethylparaphenylenediamine, 2,5-diaminophenylethanol, paraaminophenol, 2-chloro-4-aminophenol, 3-chloro-4-aminophenol, N-methylparaaminophenol and also the salts of the abovementioned compounds, such as the sulphates and hydrochlorides.

The compositions according to the invention can also contain additional couplers other than those of the formula (I), in particular metadiphenols, metaaminophenols, metadiamines or heterocyclic couplers and their acid salts.

Examples of metaaminophenols are: metaaminophenol, 2-methyl-5-aminophenol, 2-methyl-5-N-methylaminophenol, 2-methyl-5-N-β-hydroxyethylaminophenol, 2-methyl-5-N-carbamylmethylaminophenol and 2-methyl-5-N-acetylaminophenol. Examples of metadiphenols are resorcinol and 2-methylresorcinol. Examples of metadiamines are: 2,4-diaminophenoxyethanol, 2,4-diaminophenoxyethylamine, 1-(2',4'-diaminophenoxy)propane-2,3-diol and 2-N-β-hydroxyethylamino-4-aminoanisole. 2,6-Diaminopyridine is an example of a heterocyclic coupler.

The dyeing compositions according to the invention may also contain at least one direct dyestuff, particularly nitro dyestuffs of the benzene series, anthraquinone dyestuffs, indophenols or indoanilines. Examples of direct dyestuffs are 2-methyl-4-amino-5-nitrophenol, 3-N-methylamino-4-nitrophenoxyethanol, 2-N-β-hydroxyethylamino-5-nitroanisole, 2-amino-3-nitrophenol, 3-nitro-4-N-β-hydroxyethylaminophenol, 3-nitro-4-N'-methylamino-N,N-di-β-hydroxyethylaniline, 3-nitro-4-amino-N-β-hydroxyethylaniline, 2-methyl-4-amino-5-nitro-N-β-hydroxyethylaniline and 1,4,5,8-tetraaminoanthraquinone.

In a preferred embodiment, the dyeing composition according to the invention contains from 0.01% to 4% by weight of compound(s) of the formula (I) (and/or of its (their) acid salts), relative to the total weight of the composition.

The cosmetic vehicle of the composition according to the invention comprises at least one customary adjuvant, for example water, solvents, penetrating agents, surface-active agents, thickeners, antioxidants, alkalizing or acidifying agents, sequestering agents, perfumes, film-forming products and treating agents.

The pH of the composition according to the invention is preferably from 8 to 11.5. Examples of alkalizing agents are: aqueous ammonia, alkylamines such as ethylamine or triethylamine, alkanolamines such as mono-, di- or triethanolamine, alkylalkanolamines such as methyldiethanolamine, hydroxides of sodium or potassium and carbonates of sodium, potassium or ammonium. Examples of acidifying agents are: lactic acid, acetic acid, tartaric acid and phosphoric acid.

Anionic, cationic, non-ionic or amphoteric surface-active agents, or mixtures thereof, can be used according to the invention. Examples of surface-active agents are: alkylbenzenesulphonates, alkylnaphthalenesulphonates, sulphates, ether-sulphates and sulphonates of fatty alcohols, quaternary ammonium salts such as trimethylcetylammonium bromide and cetylpyridinium bromide, fatty acid diethanolamides and polyethoxylated or polyglycerolated acids, alcohols or alkylphenols. Preferably, the surface-active agents are present in the composition according to the invention in a proportion of from 0.5 to 55% by weight and advantageously of from 4 to 40% by weight, relative to the total weight of the composition.

Organic solvents can also be added to the composition according to the invention, for example ethanol, isopropanol, glycerol, glycols and their ethers, such as 2-butoxyethanol, ethylene glycol, propylene glycol, the monoethyl ether and the monomethyl ether of diethylene glycol, and analogous solvents. The solvents can advantageously be present in the composition in a proportion from 1 to 40% by weight and preferably of from 5 to 30% by weight, relative to the total weight of the composition.

Examples of thickening products which can be added to the composition according to the invention are sodium alginate, gum arabic, cellulose derivatives such as methylcellulose, hydroxyethylcellulose, hydroxypropylmethylcellulose and the sodium salt of carboxymethylcellulose, and acrylic acid polymers; it is also possible to use inorganic thickeners such as bentonite. Preferably, the thickeners are present in a proportion from 0.5 to 5% by weight, relative to the total weight of the composition, and advantageously from 0.5 to 3% by weight.

Examples of antioxidants which can be added to the composition according to the invention are sodium sulphite, thioglycolic acid, sodium bisulphite, ascorbic acid and hydroquinone. These antioxidants are preferably present in the composition in a proportion of from 0.05 to 1.5% by weight, relative to the total weight of the composition.

As the dyeing composition according to the invention is an oxidative dyeing composition, it generally contains, at the time of use, oxidizing agents such as hydrogen peroxide, urea peroxide or per-salts such as ammonium persulphate.

The dyeing composition according to the invention may, for example, be presented in the form of a liquid, cream, gel or an aerosol or in any other form suitable for dyeing keratin fibres.

The present invention also provides a new hair-dyeing process, in which, at the time of use, a sufficient quantity of oxidizing agent(s) is mixed with a dyeing composition as defined above, the mixture is left to act on the hair for a period, preferably from 10 to 45 minutes and preferably at a temperature from 10° to 50° C., and the hair is rinsed, optionally washed and rinsed again, and dried.

An advantage of the couplers of the formula (I) is that, depending on the structure of the coupler and the associated oxidation base, indoanilines or indophenols can be formed on the hair in an oxidizing alkaline medium, for example in an ammoniacal medium in the presence of hydrogen per oxide. These indoanilines or indophenols are capable of giving the hair various colourations, for example, yellow, red, purple or blue. Thus it is possible to obtain the majority of possible hues within the range of colourations. To illustrate this property, a few examples of colourations covering the whole range of shades are indicated in Table I below.

TABLE I

| Association of coupler (I) + oxidation base (VI) in an ammoniacal medium + $H_2O_2$ | Colouration |
|---|---|
| 2-Hydroxy-4-aminophenoxyethanol hydrate and paraaminophenol | Orange |
| 2-Hydroxy-4-aminophenoxyethanol hydrate and paraphenylenediamine | Red |
| 2-Hydroxy-4-N—ethylaminophenoxyethanol and paratoluylenediamine | Red-purple |
| 2-Hydroxy-4-acetylaminophenoxyethanol and paraphenylenediamine | Purple |
| 2-Hydroxy-4-acetylaminophenoxyethanol and paratoluylenediamine | Purple-blue |
| 2-Hydroxy-4-acetylaminophenoxyethanol and N,N—di-$\beta$-hydroxyethylparaphenylenediamine | Blue |

Another advantage of the couplers of the formula (I) is the fact that, at least in some cases, if they are associated with equimolecular quantities with certain oxidation bases, they make it possible to obtain dark colourations which are essential for obtaining dyes corresponding to natural colourations, and which those skilled in the art call "the background". Hitherto, the background has generally been obtained by means of paraphenylenediamines taken by themselves in an oxidizing medium and the couplers were only involved, in association with oxidation bases, for shading the background. By contrast, the couplers of the formula (I) make it possible, in association with oxidation bases, to produce a background; this is particularly advantageous because the couplers according to the invention are substantially harmless and give rise to non-mutagenic indoanilines and indophenols. These advantages are not always achieved with the background products previously used. Natural dark hues (for example more or less coppery chestnut or purplish grey or black) are obtained, in particular, when the couplers of the formula (I) in which the radical R represents a hydrogen atom or a substituted or unsubstituted alkyl radical are associated in equimolecular quantities with paraphenylenediamines and paraaminophenols. For example, the association of paraphenylenediamine and 2-hydroxy-4-aminophenoxyethanol in equimolecular quantities gives a chestnut colouration on 90% naturally white hair, whereas an analogous coupler of the state of the art, namely 2-methyl-5-aminophenol, leads to an intense purplish red colouration under the same conditions and the association of N,N-di-$\beta$-hydroxyethylparaphenylenediamine in equimolecular quantities with the same coupler of the formula (I) as in the previous example leads to a black colouration with violet highlights on bleached hair. Replacement of the coupler of the formula (I) with the same coupler of the state of the art as in the previous example leads to a very bright purple colouration under the same conditions. This possibility of producing dark backgrounds is unexpected for those skilled in the art, who normally use couplers as toners, and it is particularly advantageous on account of the substantial harmlessness of the couplers and of the indoanilines or indophenol compounds to which they lead. As is known, those skilled in the art are unable to predict, from the similar compounds of the state of the art, what the mutagenic characteristics of a new compound will be. It has been found, according to the invention, that the new compounds of the formula (I) are not mutagenic (AMES test on SALMONELLA TYPHIMURIUM (strains TA 1535, 1537, 1538, 98, 100) with or without activation ($S_9$ support activated with arochlor)). Furthermore, it has been found that the compounds of the formula (I) give rise to non-mutagenic indoanilines and indophenols in the oxidizing alkaline medium in which they are used during hair dyeing, and this is totally surprising when it is known that the indoanilines or indophenols obtained from the similar couplers described in U.S. Pat. No. 3,834,866 are particularly mutagenic (CHEMICAL ABSTRACT SELECTS—PROTON MAGNETIC RESONANCE, Volume 18, 1981, page 1, 95: 75096f).

Couplers of formula (I) make it possible to obtain colourations which are substantially stable to light, weather and washing. This quality is particularly marked for the couplers of the formula (I) in which R represents a hydrogen atom or an alkyl, hydroxyalkyl or carbamylalkyl radical. In particular, it is very desirable to obtain colourations which are both warm (coppery mahogany) and of very good quality. This is the case when 2-hydroxy-4-aminophenoxyethanol is associated with paraaminophenols.

The invention will be further described with the following Examples:

EXAMPLE 1

Preparation of 2-hydroxy-4-aminophenoxyethanol hydrate

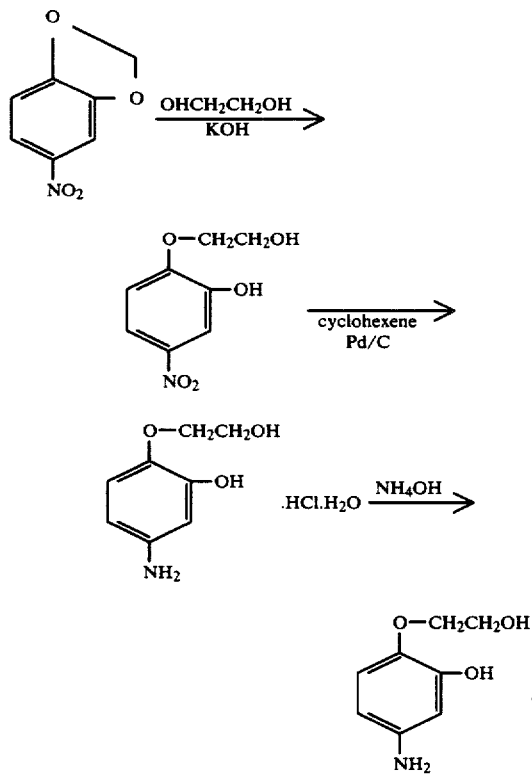

First Step: Preparation of 2-hydroxy-4-nitrophenoxyethanol 0.2 mol (11.2 g) of potassium hydroxide is dissolved in 167 ml of ethylene glycol in a boiling water bath. 0.1 mol (16.7 g) of 3,4-methylenedioxynitrobenzene is added, with stirring, the temperature being kept in the region of 100° C. After heating for two hours, the reaction medium is cooled to −5° C. The expected product crystallizes in the form of the potassium phenate. The phenate is filtered off and then redissolved in 250 ml of water, and the solution is acidified to pH=6 with concentrated hydrochloric acid. The 2-hydroxy-4-nitrophenoxyethanol precipitates. After filtration, washing with water and drying in vacuo, the expected product melts at 158° C.

Analysis of the product obtained gives the following results:

| ANALYSIS | CALCULATED FOR $C_8H_9NO_5$ | FOUND |
|---|---|---|
| C % | 48.24 | 48.34 |
| H % | 4.52 | 4.56 |
| N % | 7.04 | 7.05 |
| O % | 40.20 | 40.10 |

Second Step: Preparation of 2-hydroxy-4-aminophenoxyethanol hydrochloride monohydrate 0.03 mol (5.97 g) of 2-hydroxy-4-nitrophenoxyethanol is dissolved in 24 ml of absolute ethanol to which 12 ml of cyclohexene have been added, and 3 g of Pd/C (palladium-on-charcoal containing 10% by weight of palladium) are then added as a catalyst. After this mixture has been heated under reflux for two hours, the reaction medium is filtered in order to remove the catalyst, and the filtrate is collected in 10 ml of iced ethanol saturated with hydrogen chloride. The 2-hydroxy-4-aminophenoxyethanol hydrochloride monohydrate precipitates. It is filtered off, washed with a small quantity of ethanol and recrystallized from 6N hydrochloric acid. After drying in vacuo, the hydrochloride monohydrate melts with decomposition at 200° C.

Analysis of the product obtained gives the following results:

| ANALYSIS | CALCULATED FOR $C_8H_{11}NO_3.HCl.H_2O$ | FOUND |
|---|---|---|
| C % | 42.95 | 42.88 |
| H % | 6.26 | 6.25 |
| N % | 6.26 | 6.26 |
| O % | 28.64 | 28.45 |
| Cl % | 15.88 | 16.04 |

Third Step: Preparation of 2-hydroxy-4-aminophenoxyethanol hydrate 7.7 g of the hydrochloride obtained in the previous step are dissolved in 35 ml of cold water, and aqueous ammonia is added to pH=6. The expected product precipitates. It is filtered off, washed with water and dried in vacuo. It melts at 102° C.

Analysis of the product obtained gives the following results:

| ANALYSIS CALCULATED FOR $C_8H_{11}NO_3.H_2O$ | FOUND |
|---|---|
| C % 51.34 | 51.44 |
| H % 6.95 | 6.87 |
| N % 7.49 | 7.35 |
| O % 34.22 | 33.95 |

EXAMPLE 2

A different process for the preparation of 2-hydroxy-4-aminophenoxyethanol hydrate and the corresponding hydrochloride 17 g of iron powder are added to 80 ml of water to which 1 ml of acetic acid has been added. The mixture is heated to 95° C., with stirring, and 0.07 mol (13.9 g) of 2-hydroxy-4-nitrophenoxyethanol, obtained at the end of the first step of Example 1, is added gradually. When the addition has ended, the temperature is kept at 95° C. for 15 minutes, 5 ml of water containing 1 g of dissolved sodium carbonate are then added dropwise and the boiling reaction medium is filtered. Cooling of the filtrate causes precipitation of the expected product. It is filtered off, washed with water and dried over $P_2O_5$. It melts at 100° C. It is purified by conversion to the hydrochloride. This is done by dissolving the product in 40 ml of ethanol and treating this solution with 20 ml of ethanol saturated with hydrogen chloride. The 2-hydroxy-4-aminophenoxyethanol hydrochloride precipitates. It is filtered off, washed with a small quantity of ethanol containing hydrogen chloride and dried. It melts with decomposition at 200° C.

EXAMPLE 3

Preparation of 2-hydroxy-4-N-ethylaminophenoxyethanol

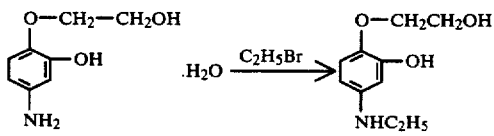

0.134 mol (25 g) of 2-hydroxy-4-aminophenoxyethanol hydrate, obtained at the end of Example 1, is dissolved in 100 ml of absolute ethanol. 0.267 mol (20.3 ml) of ethyl bromide is added and the reaction medium is heated at 60° C. for 6 hours. The ethanol is then driven off in vacuo and the residue is dissolved in 50 ml of water. The aqueous solution is neutralized with aqueous ammonia in order to precipitate the expected product. This product is filtered off, washed with iced water, dried in vacuo and recrystallized from ethyl acetate. It melts at 119° C.

Analysis of the product obtained gives the following results:

| ANALYSIS | CALCULATED FOR $C_{10}H_{15}NO_3$ | FOUND |
|---|---|---|
| C % | 60.91 | 60.83 |
| H % | 7.61 | 7.61 |
| N % | 7.11 | 6.99 |
| O % | 24.37 | 24.10 |

EXAMPLE 4

Preparation of 2-hydroxy-4-N-β-hydroxyethylaminophenoxyethanol

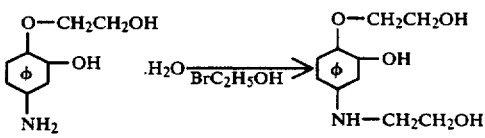

0.05 mol (9.35 g) of 2-hydroxy-4-aminophenoxyethanol hydrate, obtained in Example 1, is dissolved in 47 ml of absolute ethanol. 0.1 mol (12.5 g) of glycol bromohydrin is added and the reaction medium is heated for 6 hours in a boiling water bath. It is then evaporated to dryness under 17.3 mbar. The only residue is dissolved in 50 ml of water. The aqueous solution is subsequently neutralized with aqueous ammonia and then left to stand overnight at 0° C. The 2-hydroxy-4-N-β-hydroxyethylaminophenoxyethanol which has precipitated in the form of crystals is filtered off. After recrystallization from 95° ethanol and drying in vacuo, the product melts at 151° C.

Analysis of the product obtained gives the following results:

| ANALYSIS | CALCULATED FOR $C_{10}H_{15}NO_4$ | FOUND |
|---|---|---|
| C % | 56.33 | 56.18 |
| H % | 7.09 | 7.10 |
| N % | 6.57 | 6.43 |
| O % | 30.01 | 29.93 |

EXAMPLE 5

Preparation of N-(2-hydroxy-4-aminophenoxyethyl)acetamide

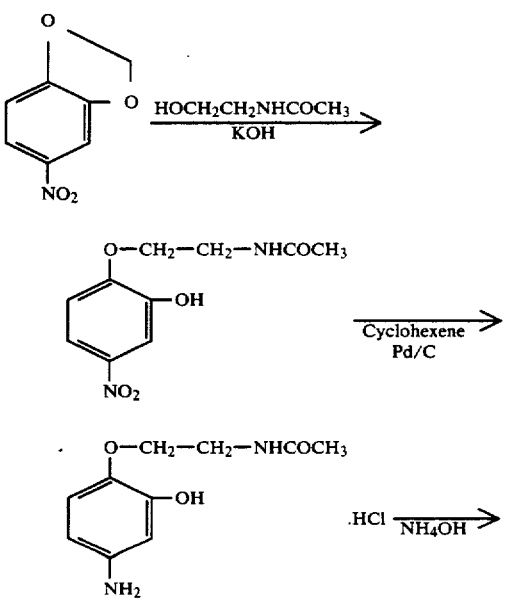

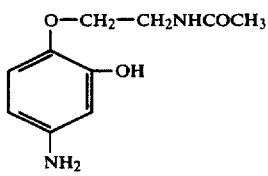

First Step: Preparation of N-(2-hydroxy-4-nitrophenoxyethyl)acetamide 0.05 mol (8.35 g) of 3,4-methylenedioxynitrobenzene is introduced into 42 ml of N-acetylethanolamine. The mixture is heated to the region of 100° C., with stirring, and 0.055 mol (3.7 ml) of 15N potassium hydroxide solution is then added. After heating for one hour, 0.050 mol (3.3 ml) of 15N potassium hydroxide solution is added and the reaction medium is stirred at 100° C. for a further 3 hours and then poured onto 120 g of crushed ice. The unreacted starting material, which is insoluble in an alkaline medium, is filtered off. The filtrate is then acidified to pH=5.6 with hydrochloric acid in order to precipitate the expected product. It is filtered off, washed with water and dried in vacuo. It melts at 165° C.

Analysis of the product obtained gives the following results:

| ANALYSIS | CALCULATED FOR $C_{10}H_{12}N_2O_5$ | FOUND |
| --- | --- | --- |
| C % | 50.00 | 49.86 |
| H % | 5.00 | 4.96 |
| N % | 11.67 | 11.62 |
| O % | 33.33 | 33.20 |

Second Step: Preparation of N-(2-hydroxy-4-aminophenoxyethyl)acetamide 0.0217 mol (5.2 g) of the nitro derivative obtained in the previous step is introduced into 10.5 ml of cyclohexene. 2.6 g of Pd/C (palladium-on-charcoal containing 10% by weight of palladium) are added as a catalyst and the mixture is then heated under reflux for two hours. The reaction medium is filtered in order to remove the catalyst, the filtrate being collected in 11 ml of ethanol saturated with hydrogen chloride and cooled in solid carbon dioxide. The expected product precipitates in the form of the hydrochloride. This hydrochloride is filtered off and redissolved in 8 ml of water, and the pH is brought to 6.2 with aqueous ammonia in order to precipitate the N-(2-hydroxy-4-aminophenoxyethyl)acetamide. The product is filtered off, washed with water and dried in vacuo. It melts at 134° C.

Analysis of the product obtained gives the following result:

| ANALYSIS | CALCULATED FOR $C_{10}H_{14}N_2O_3$ | FOUND |
| --- | --- | --- |
| C % | 57.13 | 57.83 |
| H % | 6.71 | 6.73 |
| N % | 13.33 | 13.25 |
| O % | 22.83 | 23.00 |

EXAMPLE 6

Preparation of N-methyl-N-(2-hydroxy-4-aminophenoxyethyl)acetamide

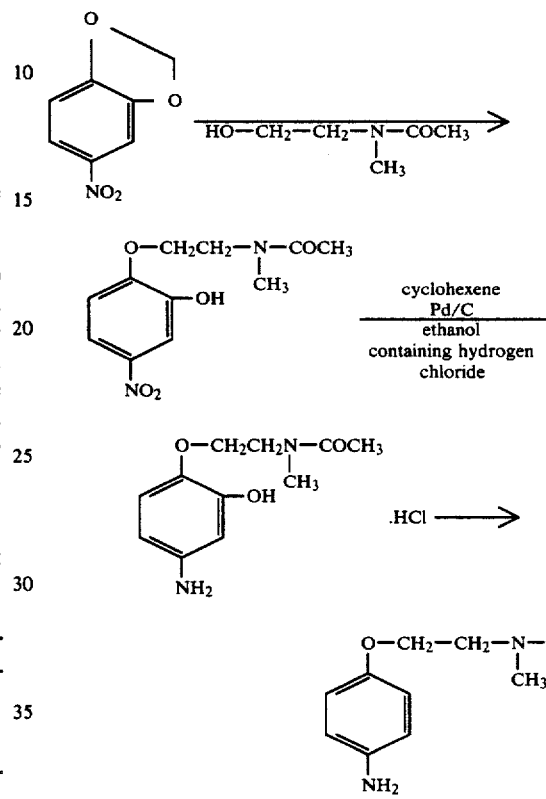

First Step: Preparation of N-methyl-N-(2-hydroxy-4-nitrophenoxyethyl)acetamide 0.1 mol (16.7 g) of 3,4-methylenedioxynitrobenzene is introduced into 67 ml of N-methyl-N-acetylethanolamine. The mixture is heated to the region of 100° C., with stirring, and 11 ml of 15N potassium hydroxide solution are then added. After stirring for 4 hours at 100° C., the reaction medium is poured onto 200 g of crushed ice. The unreacted starting material, which is insoluble in an alkaline medium, is removed by filtration. The filtrate is then brought to a pH of 5 with hydrochloric acid. The expected nitro product which has precipitated is filtered off. After washing with water, drying and recrystallization from a 50/50 ethyl acetate/ethanol mixture, the product melts at 158° C.

Analysis of the product obtained gives the following results:

| ANALYSIS | CALCULATED FOR $C_{11}H_{14}N_2O_5$ | FOUND |
| --- | --- | --- |
| C % | 51.97 | 51.91 |
| H % | 5.55 | 5.51 |
| N % | 11.02 | 11.14 |
| O % | 31.46 | 31.32 |

Second Step: Preparation of N-methyl-N-(2-hydroxy-4-aminophenoxyethyl)acetamide 0.0275 mol (7 g) of the nitro derivative obtained by the process of the first step is introduced into 35 ml of absolute ethanol to which 14 ml of cyclohexene have been added. 3.5 g of 10% Pd/C are added as a catalyst and the mixture is then heated under reflux for 4 hours. The reaction medium is filtered in order to remove the catalyst, the filtrate being collected in 14 ml of ethanol saturated with hydrogen chloride and cooled in solid carbon dioxide. After the addition of ether, the expected product precipitates in the form of crystals of the hydrochloride. This hydrochloride is filtered off and then dissolved in 7 ml of water. Aqueous ammonia is added to a pH of 6.5. The expected product precipitates. It is filtered off, washed with water and dried in vacuo. After recrystallization from alcohol, the expected products melts at 102° C.

Analysis of the product obtained gives the following results:

| ANALYSIS | CALCULATED FOR $C_{11}H_{16}N_2O_3$ | FOUND |
|---|---|---|
| C % | 58.91 | 58.86 |
| H % | 7.19 | 7.25 |
| N % | 12.49 | 12.55 |
| O % | 21.40 | 21.32 |

EXAMPLE 7

Preparation of 2-hydroxy-4-aminophenoxyethylamine dihydrochloride

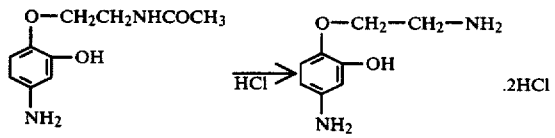

10 g of N-(2-hydroxy-4-aminophenoxyethyl)acetamide, obtained in Example 5, are introduced into 50 ml of hydrochloric acid (d=1.18) and the mixture is then heated to the reflux temperature. After heating for about twenty minutes, the reaction medium is homogeneous. Heating is continued for five hours. The 2-hydroxy-4-aminophenoxyethylamine dihydrochloride crystallizes on cooling of the hydrochloric acid solution. It is filtered off, washed with a small quantity of ethanol and dried in vacuo. It melts with decomposition above 260° C.

Analysis of the product obtained gives the following results:

| ANALYSIS | CALCULATED FOR $C_8H_{12}N_2O_2.2HCl$ | FOUND |
|---|---|---|
| C % | 39.83 | 39.75 |
| H % | 5.81 | 5.85 |
| N % | 11.62 | 11.61 |
| O % | 13.28 | 13.38 |
| Cl % | 29.46 | 29.35 |

EXAMPLE 8

Preparation of 2-hydroxy-4-acetylaminophenoxyethanol

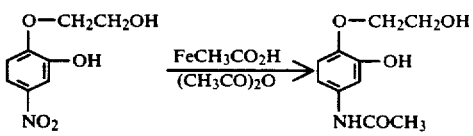

17 g of iron powder are added to 75 ml of water to which 1 ml of acetic acid has been added. This mixture is heated to 95° C. and 0.075 mol (15 g) of 2-hydroxy-4-nitrophenoxyethanol, obtained at the end of the first step of Example 1, is then added gradually over a period of 10 minutes, with stirring. When the addition has ended, heating is maintained for a further 15 minutes and 5 ml of a 20% by weight aqueous solution of sodium carbonate are added dropwise. The boiling reaction medium is filtered in order to remove the ferric sludge, the filtrate being collected in 8.5 ml of acetic anhydride. After cooling of the filtrate, the 2-hydroxy-4-acetylaminophenoxyethanol which has crystallized is filtered off and washed with water. After recrystallization from dioxane and drying in vacuo, it melts at 162° C.

Analysis of the product obtained gives the following results:

| ANALYSIS | CALCULATED FOR $C_{10}H_{13}NO_4$ | FOUND |
|---|---|---|
| C % | 56.87 | 57.01 |
| H % | 6.16 | 6.11 |
| N % | 6.63 | 6.69 |
| O % | 30.33 | 30.47 |

EXAMPLE 9

Preparation of 2-hydroxy-4-N-carbethoxyaminophenoxyethanol

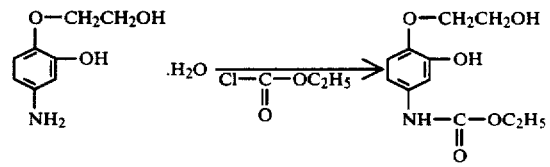

0.05 mol (9.35 g) of 2-hydroxy-4-aminophenoxyethanol hydrate, obtained in Example 1, is dissolved in 37.5 ml of dioxane under reflux. 2.75 g of calcium carbonate are added and 0.055 mol (6 g) of ethyl chloroformate is added gradually, with stirring, reflux being maintained. When the addition of the ethyl chloroformate has ended, reflux is maintained for 30 minutes and the boiling reaction medium is then filtered in order to remove the inorganic salts. On cooling of the filtrate, the expected product precipitates in the form of crystals. It is filtered off and then recrystallized from ethanol. After drying in vacuo, it melts at 145° C.

Analysis of the product obtained gives the following results:

| ANALYSIS | CALCULATED FOR $C_{11}H_{15}NO_5$ | FOUND |
|---|---|---|
| C % | 54.77 | 54.75 |

| ANALYSIS | CALCULATED FOR C₁₁H₁₅NO₅ | FOUND |
|---|---|---|
| H % | 6.27 | 6.32 |
| N % | 5.81 | 5.77 |
| O % | 33.16 | 33.05 |

EXAMPLE 10

Preparation of
1-(2-hydroxy-4-aminophenoxy)propane-2,3-diol

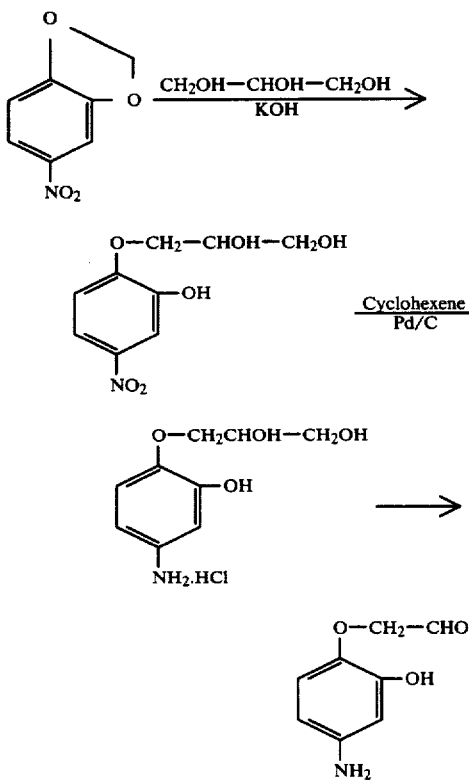

First Step: Preparation of 1-(2-hydroxy-4-nitrophenoxy)propane-2,3-diol 0.3 mol (19.8 g) of 85% by weight potassium hydroxide pellets is dissolved in 210 ml of glycerol, and 0.25 mol (41.75 g) of 3,4-methylenedioxynitrobenzene is then added, with stirring. After heating for one and a half hours in the region of 110° C., the reaction medium is poured into 1.5 liters of iced water. The mixture is filtered in order to remove a small quantity of starting material. The filtrate is acidified to pH=4 with hydrochloric acid and then treated with 10 g of vegetable charcoal. After stirring for a few minutes at ambient temperature and removal of the vegetable charcoal by filtration, the solution is left to stand overnight at 0° C. and the expected product which has crystallized is then filtered off. After recrystallization from ethanol and drying in vacuo, the product melts at 148° C.

Analysis of the product obtained gives the following results:

| ANALYSIS | CALCULATED FOR C₉H₁₁NO₆ | FOUND |
|---|---|---|
| C % | 47.16 | 47.35 |
| H % | 4.80 | 4.80 |
| N % | 6.11 | 6.01 |
| O % | 41.92 | 41.74 |

Second Step: Preparation of 1-(2-hydroxy-4-aminophenoxy)propane-2,3-diol hydrochloride 0.05 mol (11.45 g) of 1-(2-hydroxy-4-nitrophenoxy)-propane-2,3-diol, obtained in the previous step, is dissolved in 50 ml of absolute ethanol to which 15 ml of cyclohexene have been added, and 5 g of Pd/C (palladium-on-charcoal containing 10% by weight of palladium) are then added as a catalyst. After this mixture has been heated under reflux for two hours, the reaction medium is filtered in order to remove the catalyst, and the filtrate is collected in 15 ml of iced ethanol saturated with hydrogen chloride. The expected hydrochloride precipitates. It is filtered off, washed with a small quantity of iced ethanol and dried in vacuo. It melts with decomposition at 178° C.

Analysis of the product obtained gives the following results:

| ANALYSIS | CALCULATED FOR C₉H₁₃NO₄.HCl | FOUND |
|---|---|---|
| C % | 45.86 | 45.78 |
| H % | 5.94 | 5.93 |
| N % | 5.94 | 5.90 |
| O % | 27.18 | 27.05 |
| Cl % | 15.07 | 15.09 |

Third Step: Preparation of 1-(2-hydroxy-4-aminophenoxy)propane-2,3-diol 0.0936 mol (22 g) of the hydrochloride obtained in the second step is dissolved in 90 ml of water. Aqueous ammonia is added until the solution is neutral. The 1-(2-hydroxy-4-aminophenoxy)propane-2,3-diol precipitates. The product is filtered off, washed with water and dried in vacuo. It melts at 141° C.

Analysis of the product obtained gives the following results:

| ANALYSIS | CALCULATED FOR C₉H₁₃NO₄ | FOUND |
|---|---|---|
| C % | 54.27 | 54.35 |
| H % | 6.53 | 6.56 |
| N % | 7.03 | 7.00 |
| O % | 32.16 | 31.89 |

EXAMPLE 11

Preparation of
1-(2-hydroxy-4-acetylaminophenoxy)propane-2,3-diol

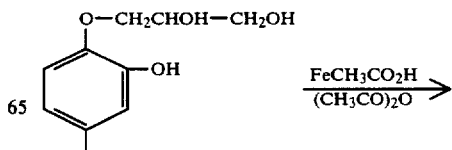

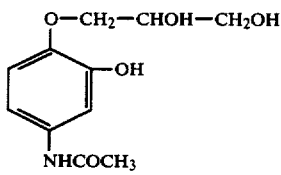

12.5 g of iron powder are added to 60 ml of water to which 2 ml of acetic acid have been added. The mixture is heated to 95° C., with stirring, and 1-(2-hydroxy-4-nitrophenoxy)propane-2,3-diol, obtained at the end of the first step of Example 9, is added gradually. When the addition has ended, heating is maintained for a further 30 minutes and 15 ml of water containing 2 g of dissolved sodium carbonate are then added dropwise; the boiling reaction medium is then filtered in order to remove the ferric sludge. On cooling of the filtrate, the 1-(2-hydroxy-4-acetylaminophenoxy)propane-2,3-diol precipitates in the form of crystals. It is filtered off, washed with water and recrystallized from absolute ethanol. After drying in vacuo, it melts at 162° C.

Analysis of the product obtained gives the following results:

| ANALYSIS | CALCULATED FOR C₁₁H₁₅NO₅ | FOUND |
|---|---|---|
| C % | 54.77 | 54.87 |
| H % | 6.22 | 6.22 |
| N % | 5.81 | 5.86 |
| O % | 33.19 | 33.00 |

EXAMPLE 12

Preparation of 2-hydroxy-4-ureidophenoxyethanol

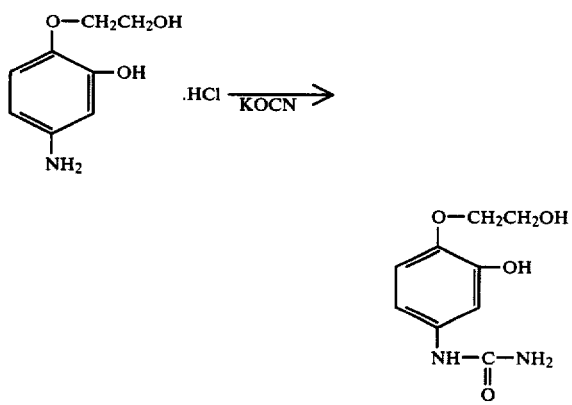

0.03 mol (6.16 g) of 2-hydroxy-4-aminophenoxyethanol hydrochloride is dissolved in 34 ml of water at 15° C. 0.03 mol (2.43 g) of potassium isocyanate dissolved in 7.5 ml of water is added to this solution, with stirring. The temperature of the reaction medium rises to 25° C. After stirring for 30 minutes, the expected product which has precipitated is filtered off. It is washed with a normal solution of hydrochloric acid and then with water. After recrystallization from acetic acid and drying in vacuo, the product melts at 191° C.

| ANALYSIS | CALCULATED FOR C₉H₁₂N₂O₄ | FOUND |
|---|---|---|
| C % | 50.34 | 50.75 |
| H % | 5.70 | 5.72 |
| N % | 13.20 | 13.30 |
| O % | 30.16 | 30.45 |

EXAMPLE 12A

Preparation of N-methyl, N-[(2-hydroxy-4-acetamido)phenoxyethyl]acetamide

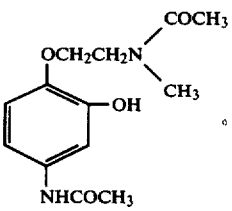

0.045 mol (1 g) of product prepared in Example 6 is made into a suspension with 4 ml dioxane. 0.47 ml of acetic anhydride is then added. At the end of the exothermic reaction, 20 ml water is added. After drying and then redispersing in the water, the product is dried under reduced pressure. After recrystallisation from 11 ml absolute ethanol and drying under reduced pressure, the product melts at 184° C.

Analysis of the product obtained gives the following results.

| ANALYSIS | CALCULATED FOR C₁₃H₁₈N₂O₄ | FOUND |
|---|---|---|
| C % | 58.63 | 58.43 |
| H % | 6.81 | 6.90 |
| N % | 10.52 | 10.66 |

EXAMPLE 13

The following dyeing composition is prepared:

| | |
|---|---|
| 2-Hydroxy-4-aminophenoxyethanol hydrate | 0.026 g |
| Paraphenylenediamine | 0.015 g |
| 2-Butoxyethanol | 6 g |
| Hydroxyethylcellulose | 2 g |
| Ammonium lauryl-sulphate | 5 g |
| Monoethanolamine | 2 g |
| Ethylenediaminetetraacetic acid sold under the name "TRILON B" | 0.5 g |
| Thiolactic acid | 0.4 g |
| Water q.s. | 100 g |

The pH of the composition is equal to 9.5.

60 g of 20 volume hydrogen peroxide are added at the time of use.

When applied for 45 minutes at 28° C. to hair which has been bleached white, this mixture imparts to the hair, after rinsing and shampooing, a pinkish beige colouration.

EXAMPLE 14

The following dyeing composition is prepared:

| | |
|---|---|
| 2-Hydroxy-4-aminophenoxyethanol hydrate | 0.467 g |
| Paraphenylenediamine | 0.27 g |
| Oleyl alcohol ethoxylated with 2 mol of ethylene oxide | 4.5 g |
| Oleyl alcohol ethoxylated with 4 mol of | |

-continued

| | |
|---|---|
| ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriamine-pentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.6.

100 g of 20 volume hydrogen peroxide are added at the time of use.

This mixture is applied for 20 minutes at 30° C. to 90% naturally white hair; it imparts to the hair, after rinsing and shampooing, a reddish chestnut colouration.

EXAMPLE 15

| | |
|---|---|
| 2-Hydroxy-4-aminophenoxyethanol hydrate | 1.73 g |
| Paratoluylenediamine dihydrochloride | 1.8 g |
| Nonylphenol containing 9 mol of ethylene oxide, sold under the name "CEMULSOL NP$_9$" by "RHONE POULENC" | 24 g |
| Nonylphenol containing 4 mol of ethylene oxide, sold under the name "CEMULSOL NP$_4$" by "RHONE POULENC" | 21 g |
| Oleic acid | 4 g |
| 2-Butoxyethanol | 3 g |
| Ethanol (96°) | 10 g |
| Pentasodium salt of diethylenetriaminepenta-acetic acid, sold under the name "MASQUOL DTPA" | 2.5 g |
| Sodium bisulphite solution (35° Bé) | 1 g |
| Aqueous ammonia (22° Bé) | 12 g |
| Water q.s. | 100 g |

The pH of the composition is equal to 10.0.

120 g of 20 volume hydrogen peroxide are added at the time of use.

When applied for 15 minutes at 28° C. to 90% naturally white hair, this mixture imparts to the hair, after rinsing and shampooing, a very dark purplish red hue.

EXAMPLE 16

The following dyeing composition is prepared:

| | |
|---|---|
| 2-Hydroxy-4-aminophenoxyethanol hydrate | 1.04 g |
| 2-Chloroparaphenylenediamine sulphate | 1.346 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepenta-acetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.6.

100 g of 20 volume hydrogen peroxide are added at time of use.

When applied for 30 minutes at 29° C. to 90% naturally white hair, this mixture imparts to the hair, after rinsing and shampooing, a reddish coppery chestnut colouration.

EXAMPLE 17

The following dyeing composition is prepared:

| | |
|---|---|
| 2-Hydroxy-4-aminophenoxyethanol hydrate | 0.055 g |
| N,N—Di-β-hydroxyethylparaphenylenediamine dihydrochloride | 0.08 g |
| 2-Butoxyethanol | 8 g |
| Hydroxyethylcellulose | 2 g |
| Ammonium lauryl-sulphate | 5 g |
| 2-Methyl-2-aminopropan-1-ol | 2.3 g |
| Pentasodium salt of diethylenetriaminepenta-acetic acid, sold under the name "MASQUOL DTPA" | 1.5 g |
| Mercaptosuccinic acid | 1 g |
| Water q.s. | 100 g |

The pH of the composition is equal to 9.3.

60 g of 20 volume hydrogen peroxide are added at the time of use.

When applied to bleached hair for 40 minutes at 28° C., this mixture imparts to the hair, after rinsing and shampooing, a silvery grey colouration with mauve highlights.

EXAMPLE 18

The following dyeing composition is prepared:

| | |
|---|---|
| 2-Hydroxy-4-aminophenoxyethanol hydrate | 0.83 g |
| N,N—Di-β-hydroxyethylparaphenylenediamine dihydrochloride | 1.20 g |
| Acrylic acid polymer having a molecular weight of 2 to 3 million, sold under the name "CARBOPOL 934" by "GOODRICH CHEMICAL CO" | 1.5 g |
| Ethanol (96°) | 11 g |
| 2-Butoxyethanol | 5 g |
| Trimethylcetylammonium bromide | 1 g |
| Ethylenediaminetetraacetic acid sold under the name "TRILON B" | 0.1 g |
| Thioglycolic acid | 0.2 g |
| Aqueous ammonia (22° Bé) | 10 g |
| Water q.s. | 100 g |

The pH of the composition is equal to 9.8.

100 g of 20 volume hydrogen peroxide are added at the time of use.

When applied for 20 minutes at 27° C. to hair which has been bleached straw yellow, this mixture imparts to the hair, after rinsing and shampooing, a very dark violet colouration.

EXAMPLE 19

The following dyeing composition is prepared:

| | |
|---|---|
| 2-Hydroxy-4-aminophenoxyethanol hydrate | 1.595 g |
| N,N—Di-β-hydroxyethylparaphenylenediamine dihydrochloride | 2.29 g |
| Nonylphenol ethoxylated with 4 mol of ethylene oxide, sold under the name "CEMULSOL NP$_4$" by "RHONE POULENC" | 21 g |
| Nonylphenol ethoxylated with 9 mol of ethylene oxide, sold under the name "CEMULSOL NP$_9$" by "RHONE POULENC" | 24 g |
| Oleic acid | 4 g |
| 2-Butoxyethanol | 3 g |

-continued

| | |
|---|---|
| Ethanol (96°) | 10 g |
| Pentasodium salt of diethylenetriaminepenta-acetic acid, sold under the name "MASQUOL DTPA" | 2.5 g |
| Thioglycolic acid | 0.6 g |
| Aqueous ammonia (22° Bé) | 10 g |
| Water q.s. | 100 g |

The pH of the composition is equal to 9.6.

100 g of 20 volume hydrogen peroxide are added at the time of use.

When applied for 15 minutes at 30° C. to hair which has been bleached white, this mixture imparts to the hair, after rinsing and shampooing, a black colouration with purplish blue highlights.

EXAMPLE 20

The following dyeing composition is prepared:

| | |
|---|---|
| 2-Hydroxy-4-aminophenoxyethanol hydrate | 1.13 g |
| N—β-Methoxyethylparaphenylenediamine dihydrochloride | 1.43 g |
| Acrylic acid polymer having a molecular weight of 2 to 3 million, sold under the name "CARBOPOL 934" by "GOODRICH CHEMICAL CO" | 3 g |
| Ethanol (96°) | 11 g |
| 2-Butoxyethanol | 5 g |
| Trimethylcetylammonium bromide | 2 g |
| Ethylenediaminetetraacetic acid sold under the name "TRILON B" | 0.2 g |
| Aqueous ammonia (22° Bé) | 10 g |
| Sodium bisulphite solution (35° Bé) | 1 g |
| Water q.s. | 100 g |

The pH of the composition is equal to 9.6.

100 g of 20 volume hydrogen peroxide are added at the time of use.

When applied for 20 minutes at 29° C. to 100% naturally white hair, this mixture imparts to the hair, after rinsing and shampooing, a very dark purplish red colouration.

EXAMPLE 21

The following dyeing composition is prepared:

| | |
|---|---|
| 2-Hydroxy-4-aminophenoxyethanol hydrate | 0.82 g |
| 2,6-Dimethylparaphenylenediamine dihydrochloride | 0.92 g |
| Cetyl/stearyl alcohol sold under the name "ALFOL C16/18 E" by "CONDEA" | 8 g |
| Sodium cetyl/stearyl-sulphate sold under the name "LANETTE WAX E" by "HENKEL" | 0.5 g |
| Ethoxylated castor oil sold under the name "CEMULSOL B" by "RHONE POULENC" | 1 g |
| Oleic diethanolamide | 1.5 g |
| Thioglycolic acid | 0.5 g |
| Hydroquinone | 0.4 g |
| Pentasodium salt of diethylenetriaminepenta-acetic acid, sold under the name "MASQUOL DTPA" | 1 g |
| Aqueous ammonia (22° Bé) | 10 g |
| Water q.s. | 100 g |

The pH of the composition is equal to 10.2.

100 g of 20 volume hydrogen peroxide are added at the time of use.

When applied for 30 minutes at 27° C. to hair which has been bleached white, this mixture imparts to the hair, after rinsing and shampooing, a deep chestnut hue with coppery highlights.

EXAMPLE 22

The following dyeing composition is prepared:

| | |
|---|---|
| 2-Hydroxy-4-aminophenoxyethanol hydrate | 0.22 g |
| 2,5-Diaminophenoxyethanol dihydrochloride | 0.28 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepenta-acetic acid, sold under the name "MASQUOL DTPA" | 2 g |
| Thioglycolic acid | 0.5 g |
| Aqueous ammonia (22° Bé) | 10 g |
| Water q.s. | 100 g |

The pH of the composition is equal to 10.1.

100 g of 20 volume hydrogen peroxide are added at the time of use.

When applied for 35 minutes at 29° C. to hair which has been bleached white, this mixture imparts to the hair, after rinsing and shampooing, a purplish silvery grey colouration.

EXAMPLE 23

The following dyeing composition is prepared:

| | |
|---|---|
| 2-Hydroxy-4-aminophenoxyethanol hydrate | 1.71 g |
| Paraaminophenol | 1 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepenta-acetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.2.

80 g of 20 volume hydrogen peroxide are added at the time of use.

When applied for 30 minutes at 25° C. to 90% naturally white hair, this mixture imparts to the hair, after rinsing and shampooing, a copper colouration.

EXAMPLE 24

The following dyeing composition is prepared:

| | |
|---|---|
| 2-Hydroxy-4-aminophenoxyethanol hydrate | 0.91 g |
| 3-Chloro-4-aminophenol hydrochloride | 0.87 g |
| Carboxymethylcellulose | 2 g |
| Ammonium lauryl-sulphate | 5 g |
| 2-Butoxyethanol | 8 g |
| Propylene glycol | 8 g |
| Pentasodium salt of diethylenetriaminepenta-acetic acid, sold under the name "MASQUOL | |

| | |
|---|---|
| DTPA" | 2 g |
| Ammonium acetate | 1 g |
| Thioglycolic acid | 0.4 g |
| Aqueous ammonia (22° Be) | 2 g |
| Water q.s. | 100 g |

The pH of the composition is equal to 9.0.

60 g of 20 volume hydrogen peroxide are added at the time of use.

When applied for 35 minutes at 28° C. to hair which has been bleached white, this mixture imparts to the hair, after rinsing and shampooing, a light mahogany colouration.

EXAMPLE 25

The following dyeing composition is prepared:

| | |
|---|---|
| 2-Hydroxy-4-aminophenoxyethanol hydrate | 1.72 g |
| 2,5-Diaminopyridine dihydrochloride | 1.67 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.1.

100 g of 20 volume hydrogen peroxide are added at the time of use.

When applied for 40 minutes at 29° C. to 90% naturally white hair, this mixture imparts to the hair, after rinsing and shampooing, a medium chestnut hue.

EXAMPLE 26

The following dyeing composition is prepared:

| | |
|---|---|
| 2-Hydroxy-4-N—ethylaminophenoxyethanol | 0.49 g |
| Paraphenylenediamine | 0.268 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.8.

100 g of 20 volume hydrogen peroxide are added at the time of use.

When applied for 20 minutes at 30° C. to hair which has been bleached white, this mixture imparts to the hair, after rinsing and shampooing, a chestnut colouration.

EXAMPLE 27

The following dyeing composition is prepared:

| | |
|---|---|
| 2-Hydroxy-4-N—ethylaminophenoxyethanol | 1.81 g |
| Paratoluylenediamine dihydrochloride | 1.79 g |
| Nonylphenol ethoxylated with 4 mol of ethylene oxide, sold under the name "CEMULSOL NP$_4$" by "RHONE POULENC" | 21 g |
| Nonylphenol ethoxylated with 9 mol of ethylene oxide, sold under the name "CEMULSOL NP$_9$" by "RHONE POULENC" | 24 g |
| Oleic acid | 4 g |
| 2-Butoxyethanol | 3 g |
| Ethanol (96°) | 10 g |
| Pentasodium salt of diethylenetriaminepentaacetic acid, sold under the name "MASQUOL DTPA" | 2.5 g |
| Sodium bisulphite solution (35° Bé) | 1 g |
| Aqueous ammonia (22° Bé) | 12 g |
| Water q.s. | 100 g |

The pH of the composition is equal to 10.0.

120 g of 20 volume hydrogen peroxide are added at the time of use.

When applied for 15 minutes at 28° C. to hair which has been bleached white, this mixture imparts to the hair, after rinsing and shampooing, a deep chestnut colouration with purple highlights.

EXAMPLE 28

The following dyeing composition is prepared:

| | |
|---|---|
| 2-Hydroxy-4-N—ethylaminophenoxyethanol | 1.8 g |
| Paraaminophenol | 0.99 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.2.

80 g of 20 volume hydrogen peroxide are added at the time of use.

When applied for 30 minutes at 27° C. to hair which has been bleached white, this mixture imparts to the hair, after rinsing and shampooing, a golden chestnut hue.

EXAMPLE 29

The following dyeing composition is prepared:

| | |
|---|---|
| 1-(2'-Hydroxy-4'-aminophenoxy)propane-2,3-diol hydrochloride | 1.74 g |
| Paraphenylenediamine | 0.8 g |

-continued

| | |
|---|---|
| Nonylphenol ethoxylated with 4 mol of ethylene oxide, sold under the name "CEMULSOL NP₄" by "RHONE POULENC" | 21 g |
| Nonylphenol ethoxylated with 9 mol of ethylene oxide, sold under the name "CEMULSOL NP₉" by "RHONE POULENC" | 24 g |
| Oleic acid | 4 g |
| 2-Butoxyethanol | 3 g |
| Ethanol (96°) | 10 g |
| Pentasodium salt of diethylenetriaminepenta-acetic acid, sold under the name "MASQUOL DTPA" | 2.5 g |
| Sodium bisulphite solution (35° Bé) | 1 g |
| Aqueous ammonia (22° Bé) | 10 g |
| Water q.s. | 100 g |

The pH of the composition is equal to 10.2.

100 g of 20 volume hydrogen peroxide are added at the time of use.

When applied for 30 minutes at 29° C. to hair which has been bleached white, this mixture imparts to the hair, after rinsing and shampooing, a very dark purplish red colouration.

EXAMPLE 30

The following dyeing composition is prepared:

| | |
|---|---|
| 1-(2'-Hydroxy-4'-aminophenoxy)propane-2,3-diol | 1.31 g |
| 2,5-Diaminophenylethanol dihydrochloride | 1.48 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO₁₂" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepenta-acetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.05.

100 g of 20 volume hydrogen peroxide are added at the time of use.

When applied for 30 minutes at 29° C. to hair which has been bleached white, this mixture imparts to the hair, after rinsing and shampooing, a deep chestnut hue with purplish red highlights.

EXAMPLE 31

The following dyeing composition is prepared:

| | |
|---|---|
| 1-(2'-Hydroxy-4'-aminophenoxy)propane-2,3-diol hydrochloride | 0.75 g |
| 3-Chloro-4-aminophenol hydrochloride | 0.54 g |
| Nonylphenol ethoxylated with 4 mol of ethylene oxide, sold under the name "CEMULSOL NP₄" by "RHONE POULENC" | 21 g |
| Nonylphenol ethoxylated with 9 mol of ethylene oxide, sold under the name "CEMULSOL NP₉" by "RHONE POULENC" | 24 g |
| Oleic acid | 4 g |
| 2-Butoxyethanol | 3 g |
| Ethanol (96°) | 10 g |
| Pentasodium salt of diethylenetriaminepenta-acetic acid, sold under the name "MASQUOL DTPA" | 2.5 g |
| Thioglycolic acid | 0.6 g |
| Aqueous ammonia (22° Bé) | 10 g |
| Water q.s. | 100 g |

The pH of the composition is equal to 10.4.

120 g of 20 volume hydrogen peroxide are added at the time of use.

When applied for 35 minutes at 28° C. to hair which has been bleached white, this mixture imparts to the hair, after rinsing and shampooing, a pink champagne hue.

EXAMPLE 32

The following dyeing composition is prepared:

| | |
|---|---|
| 1-(2'-Hydroxy-4'-aminophenoxy)propane-2,3-diol hydrochloride | 0.294 g |
| Paraaminophenol | 0.136 g |
| Nonylphenol ethoxylated with 4 mol of ethylene oxide, sold under the name "CEMULSOL NP₄" by "RHONE POULENC" | 12 g |
| Nonylphenol ethoxylated with 9 mol of ethylene oxide, sold under the name "CEMULSOL NP₉" by "RHONE POULENC" | 15 g |
| Oleyl alcohol ethoxylated with 2 mol of ethylene oxide | 1.5 g |
| Oleyl alcohol ethoxylated with 4 mol of ethylene oxide | 1.5 g |
| Propylene glycol | 6 g |
| Ethylenediaminetetraacetic acid sold under the name "TRILON B" | 0.12 g |
| Aqueous ammonia (22° Bé) | 11 g |
| Thioglycolic acid | 0.6 g |
| Water q.s. | 100 g |

The pH of the composition is equal to 9.6.

120 g of 20 volume hydrogen peroxide are added at the time of use.

When applied for 30 minutes at 28° C. to hair which has been bleached white, this mixture imparts to the hair, after rinsing and shampooing, a light copper colouration.

EXAMPLE 33

The following dyeing composition is prepared:

| | |
|---|---|
| 1-(2'-Hydroxy-4'-aminophenoxy)propane-2,3-diol | 0.147 g |
| N,N—Di-β-hydroxyethylparaphenylenediamine dihydrochloride | 0.2 g |
| Nonylphenol ethoxylated with 4 mol of ethylene oxide, sold under the name "CEMULSOL NP₄" by "RHONE POULENC" | 21 g |
| Nonylphenol ethoxylated with 9 mol of ethylene oxide, sold under the name "CEMULSOL NP₉" by "RHONE POULENC" | 24 g |
| Oleic acid | 4 g |
| 2-Butoxyethanol | 3 g |
| Ethanol (96°) | 10 g |
| Pentasodium salt of diethylenetriaminepenta-acetic acid, sold under the name "MASQUOL DTPA" | 25 g |
| Thioglycolic acid | 0.6 g |
| Aqueous ammonia (22° Bé) | 10 g |
| Water q.s. | 100 g |

The pH of the composition is equal to 10.4.

100 g of 20 volume hydrogen peroxide are added at the time of use.

When applied for 40 minutes at 29° C. to hair which has been bleached white, this mixture imparts to the hair, after rinsing and shampooing, a wistaria mauve colouration.

EXAMPLE 34

The following dyeing composition is prepared:

| | |
|---|---|
| 2-Hydroxy-4-aminophenoxyethylamine dihydrochloride | 0.44 g |
| Paraphenylenediamine | 0.2 g |
| Nonylphenol ethoxylated with 4 mol of ethylene oxide, sold under the name "CEMULSOL NP$_4$" by "RHONE POULENC" | 21 g |
| Nonylphenol ethoxylated with 9 mol of ethylene oxide, sold under the name "CEMULSOL NP$_9$" by "RHONE POULENC" | 24 g |
| Oleic acid | 4 g |
| 2-Butoxyethanol | 3 g |
| Ethanol (96°) | 10 g |
| Pentasodium salt of diethylenetriaminepentaacetic acid, sold under the name "MASQUOL DTPA" | 2.5 g |
| Thioglycolic acid | 0.6 g |
| Aqueous ammonia (22° Bé) | 10 g |
| Water q.s. | 100 g |

The pH of the composition is equal to 10.0.

100 g of 20 volume hydrogen peroxide are added at the time of use.

When applied for 40 minutes at 29° C. to 90% naturally white hair, this mixture imparts to the hair, after rinsing and shampooing, a reddish chestnut hue.

EXAMPLE 35

The following dyeing composition is prepared:

| | |
|---|---|
| 2-Hydroxy-4-aminophenoxyethylamine dihydrochloride | 0.197 g |
| Paratoluylenediamine dihydrochloride | 0.16 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.7.

100 g of 20 volume hydrogen peroxide are added at the time of use.

When applied for 20 minutes at 29° C. to hair which has been bleached white, this mixture imparts to the hair, after rinsing and shampooing, a slightly pinkish ashen beige colouration.

EXAMPLE 36

The following dyeing composition is prepared:

| | |
|---|---|
| 2-Hydroxy-4-aminophenoxyethylamine dihydrochloride | 2.21 g |
| Paraaminophenol | 1 g |
| Acrylic acid polymer having a molecular weight of 2 to 3 million, sold under the name "CARBOPOL 934" by "GOODRICH CHEMICAL CO" | 1.5 g |
| Ethanol (96°) | 11 g |
| 2-Butoxyethanol | 5 g |
| Trimethylcetylammonium bromide | 1 g |
| Ethylenediaminetetraacetic acid sold under the name "TRILON B" | 0.1 g |
| Aqueous ammonia (22° Bé) | 10 g |
| Thioglycolic acid | 0.2 g |
| Water q.s. | 100 g |

The pH of the composition is equal to 9.7.

100 g of 20 volume hydrogen peroxide are added at the time of use.

When applied for 30 minutes at 29° C. to hair which has been bleached white, this mixture imparts to the hair, after rinsing and shampooing, a reddish copper colouration.

EXAMPLE 37

The following dyeing composition is prepared:

| | |
|---|---|
| 2-Hydroxy-4-acetylaminophenoxyethanol | 0.025 g |
| Paraphenylenediamine | 0.013 g |
| Carboxymethylcellulose | 2 g |
| Ammonium lauryl-sulphate | 5 g |
| 2-Butoxyethanol | 8 g |
| Propylene glycol | 8 g |
| Pentasodium salt of diethylenetriaminepentaacetic acid, sold under the name "MASQUOL DTPA" | 2 g |
| Thioglycolic acid | 0.4 g |
| Ammonium acetate | 1 g |
| Aqueous ammonia (22° Bé) | 5 g |
| Water q.s. | 100 g |

The pH of the composition is equal to 10.0.

60 g of 20 volume hydrogen peroxide are added at the time of use.

When applied for 30 minutes at 25° C. to hair which has been bleached white, this mixture imparts to the hair, after rinsing and shampooing, a pearlescent raw silk colouration with Parma highlights.

EXAMPLE 38

The following dyeing composition is prepared:

| | |
|---|---|
| Hydroxy-4-acetylaminophenoxyethanol | 0.105 g |
| Paraphenylenediamine | 0.054 g |
| Acrylic acid polymer having a molecular weight of 2 to 3 million, sold under the name "CARBOPOL 934" by "GOODRICH CHEMICAL CO" | 1.5 g |
| Ethanol (96°) | 11 g |
| 2-Butoxyethanol | 5 g |
| Trimethylcetylammonium bromide | 1 g |
| Ethylenediaminetetraacetic acid sold under the name "TRILON B" | 0.1 g |
| Aqueous ammonia (22° Bé) | 10 g |
| Thioglycolic acid | 0.2 g |
| Water q.s. | 100 g |

The pH of the composition is equal to 10.

100 g of 20 volume hydrogen peroxide are added at the time of use.

When applied for 35 minutes at 28° C. to hair which has been bleached white, this mixture imparts to the hair, after rinsing and shampooing, a wistaria mauve colouration.

EXAMPLE 39

The following dyeing composition is prepared:

| | |
|---|---|
| 2-Hydroxy-4-acetylaminophenoxyethanol | 0.53 g |
| Paraphenylenediamine | 0.27 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.6.

100 g of 20 volume hydrogen peroxide are added at the time of use.

When applied for 20 minutes at 30° C. to hair which has been bleached white, this mixture imparts to the hair, after rinsing and shampooing, a purple colouration.

EXAMPLE 40

The following dyeing composition is prepared:

| | |
|---|---|
| 2-Hydroxy-4-acetylaminophenoxyethanol | 158 g |
| Paraphenylenediamine | 0.81 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.3.

100 g of 20 volume hydrogen peroxide are added at the time of use.

When applied for 20 minutes at 25° C. to 90% naturally white hair, this mixture imparts to the hair, after rinsing and shampooing, an extremely dark violet colouration.

EXAMPLE 41

The following dyeing composition is prepared:

| | |
|---|---|
| 2-Hydroxy-4-acetylaminophenoxyethanol | 0.06 g |
| Paratoluylenediamine dihydrochloride | 0.054 g |
| 2-Butoxyethanol | 6 g |
| Hydroxyethylcellulose | 2 g |
| Ammonium lauryl-sulphate | 5 g |
| Thioglycolic acid | 0.5 g |
| Hydroquinone | 0.4 g |
| Monoethanolamine | 4 g |
| Water q.s. | 100 g |

The pH of the composition is equal to 10.1.

60 g of 20 volume hydrogen peroxide are added at the time of use.

When applied for 45 minutes at 28° C. to hair which has been bleached white, this mixture imparts to the hair, after rinsing and shampooing, a grey colouration.

EXAMPLE 42

The following dyeing composition is prepared:

| | |
|---|---|
| 2-Hydroxy-4-acetylaminophenoxyethanol | 0.67 g |
| Paratoluylenediamine dihydrochloride | 0.62 g |
| 2-Butoxyethanol | 8 g |
| Hydroxyethylcellulose | 2 g |
| Ammonium lauryl-sulphate | 5 g |
| Aqueous ammonia (20%) | 10 g |
| Pentasodium salt of diethylenetriaminepentaacetic acid, sold under the name "MASQUOL DTPA " | 1.5 g |
| Mercaptosuccinic acid | 1 g |
| Water q.s. | 100 g |

The pH of the composition is equal to 10.0.

60 g of 20 volume hydrogen peroxide are added at the time of use.

When applied for 30 minutes at 20° C. to hair which has been bleached white, this mixture imparts to the hair, after rinsing and shampooing, an intense violet hue.

EXAMPLE 43

The following dyeing composition is prepared:

| | |
|---|---|
| 2-Hydroxy-4-acetylaminophenoxyethanol | 1.08 g |
| Paratoluylenediamine dihydrochloride | 1.0 g |
| Cetyl/stearyl alcohol containing 15 mol of ethylene oxide, sold under the name "MERGITAL CS 15/E" by "HENKEL" | 2.5 g |
| Ammonium lauryl-sulphate (containing 30% of active ingredient) | 12 g |
| Polymer based on repeat units of the formula: | |

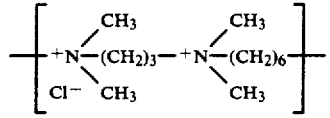

| | |
|---|---|
| | 4 g |
| Benzyl alcohol | 2 g |
| Sodium bisulphite solution (35° Bé) | 1.2 g |
| Aqueous ammonia (22° Bé) | 12 g |
| Ethylenediaminetetraacetic acid sold under the name "TRILON B" | 1 g |
| Water q.s. | 100 g |

The pH of the composition is equal to 10.0.

100 g of 20 volume hydrogen peroxide are added at the time of use.

When applied for 25 minutes at 28° C. to hair which has been bleached white, this mixture imparts to the hair, after rinsing and shampooing, an intense purplish blue colouration.

EXAMPLE 44

The following dyeing composition is prepared:

| | |
|---|---|
| 2-Hydroxy-4-acetylaminophenoxyethanol | 0.53 g |
| Chloroparaphenylenediamine sulphate | 0.60 g |
| Nonylphenol ethoxylated with 4 mol of ethylene oxide, sold under the name "CEMULSOL NP$_4$" by "RHONE POULENC" | 21 g |
| Nonylphenol ethoxylated with 9 mol of ethylene oxide, sold under the name "CEMULSOL NP$_9$" by "RHONE POULENC" | 24 g |
| Oleic acid | 4 g |
| 2-Butoxyethanol | 3 g |
| Ethanol (96°) | 10 g |
| Pentasodium salt of diethylenetriaminepentaacetic acid, sold under the name "MASQUOL-DTPA" | 2.5 g |
| Thioglycolic acid | 0.6 g |
| Aqueous ammonia (22° Bé) | 10 g |
| Water q.s. | 100 g |

The pH of the composition is equal to 10.0.

100 g of 20 volume hydrogen peroxide are added at the time of use.

When applied for 20 minutes at 30° C. to hair which has been bleached white, this mixture imparts to the hair, after rinsing and shampooing, a cyclamen purple hue.

EXAMPLE 45

The following dyeing composition is prepared:

| | |
|---|---|
| 2-Hydroxy-4-acetylaminophenoxyethanol | 0.05 g |
| N,N—Di-β-hydroxyethylparaphenylenediamine dihydrochloride | 0.0637 g |
| Nonylphenol ethoxylated with 4 mol of ethylene oxide, sold under the name "CEMULSOL NP$_4$" by "RHONE POULENC" | 21 g |
| Nonylphenol ethoxylated with 9 mol of ethylene oxide, sold under the name "CEMULSOL NP$_9$" by "RHONE POULENC" | 24 g |
| Oleic acid | 4 g |
| 2-Butoxyethanol | 3 g |
| Ethanol (96°) | 10 g |
| Pentasodium salt of diethylenetriaminepentaacetic acid, sold under the name "MASQUOL DTPA" | 2.5 g |
| Thioglycolic acid | 0.6 g |
| Aqueous ammonia (22° Bé) | 10 g |
| Water q.s. | 100 g |

The pH of the composition is equal to 10.2.

60 g of 20 volume hydrogen peroxide are added at the time of use.

When applied for 40 minutes at 30° C. to hair which has been bleached white, this mixture imparts to the hair, after rinsing and shampooing, a light blue colouration.

EXAMPLE 46

The following dyeing composition is prepared:

| | |
|---|---|
| 2-Hydroxy-4-acetylaminophenoxyethanol | 1.8 g |
| N,N—Di-β-hydroxyethylparaphenylenediamine dihydrochloride | 2.29 g |
| Nonylphenol ethoxylated with 4 mol of ethylene oxide, sold under the name "CEMULSOL NP$_4$" by "RHONE POULENC" | 21 g |
| Nonylphenol ethoxylated with 9 mol of ethylene oxide, sold under the name "CEMULSOL NP$_9$" by "RHONE POULENC" | 24 g |
| Oleic acid | 4 g |
| 2-Butoxyethanol | 3 g |
| Ethanol (96°) | 10 g |
| Pentasodium salt of diethylenetriaminepentaacetic acid, sold under the name "MASQUOL DTPA" | 2.5 g |
| Thioglycolic acid | 0.6 g |
| Aqueous ammonia (22° Bé) | 10 g |
| Water q.s. | 100 g |

The pH of the composition is equal to 9.3.

100 g of 20 volume hydrogen peroxide are added at the time of use.

When applied for 15 minutes at 25° C. to 90% naturally white hair, this mixture imparts to the hair, after rinsing and shampooing, a very intense blue colouration.

EXAMPLE 47

The following dyeing composition is prepared:
The following dyeing composition is prepared:

| | |
|---|---|
| 2-Hydroxy-4-acetylaminophenoxyethanol | 0.44 g |
| N—β-Methoxyethylparaphenylenediamine dihydrochloride | 0.5 g |
| Carboxymethylcellulose | 2 g |
| Ammonium lauryl-sulphate | 5 g |
| 2-Butoxyethanol | 8 g |
| Propylene glycol | 8 g |
| pentasodium salt of diethylenetriaminepentaacetic acid, sold under the name "MASQUOL DTPA" | 2 g |
| Thioglycolic acid | 0.4 g |
| Ammonium acetate | 1 g |
| Aqueous ammonia (22° Bé) | 12 g |
| Water q.s. | 100 g |

The pH of the composition is equal to 10.2.

100 g of 20 volume hydrogen peroxide are added at the time of use.

When applied for 15 minutes at 30° C. to 100% naturally white hair, this mixture imparts to the hair, after rinsing and shampooing, a forget-me-not blue colouration.

EXAMPLE 48

The following dyeing composition is prepared:

| | |
|---|---|
| 2-Hydroxy-4-acetylaminophenoxyethanol | 1.21 g |
| 2,6-Dimethylparaphenylenediamine dihydrochloride | 1.20 g |
| Acrylic acid polymer having a molecular weight of 2 to 3 million, sold under the name "CARBOPOL 934" by "GOODRICH CHEMICAL CO" | 1.5 g |
| Ethanol (96°) | 11 g |
| 2-Butoxyethanol | 5 g |
| Trimethylcetylammonium bromide | 1 g |
| Ethylenediaminetetraacetic acid sold under the name "TRILON B" | 0.1 g |
| Aqueous ammonia (22° Bé) | 10 g |
| Thioglycolic acid | 0.2 g |
| Water q.s. | 100 g |

The pH of the composition is equal to 10.1.

100 g of 20 volume hydrogen peroxide are added at the time of use.

When applied for 20 minutes at 30° C. to 90% naturally white hair, this mixture imparts to the hair, after rinsing and shampooing, a fairly dark violet colouration.

EXAMPLE 49

The following dyeing composition is prepared:

| | |
|---|---|
| 2-Hydroxy-4-acetylaminophenoxyethanol | 0.69 g |
| 2,5-Diaminophenoxyethanol dihydrochloride | 0.8 g |
| Cetyl/stearyl alcohol sold under the name "ALFOL C16/18 E" by "CONDEA" | 8 g |
| Sodium cetyl/stearyl-sulphate sold under the name "LANETTE WAX E" by "HENKEL" | 0.5 g |
| Ethoxylated castor oil sold under the name "CEMULSOL B" by "RHONE POULENC" | 1 g |
| Oleic diethanolamide | 1.5 g |
| Pentasodium salt of diethylenetriaminepentaacetic acid, sold under the name "MASQUOL DTPA" | 1 g |
| Hydroquinone | 0.15 g |
| Aqueous ammonia (22° Bé) | 11 g |
| Water q.s. | 100 g |

The pH of the composition is equal to 10.4.

100 g of 20 volume hydrogen peroxide are added at the time of use.

When applied for 30 minutes at 30° C. to hair which has been bleached white, this mixture imparts to the hair, after rinsing and shampooing, a purplish blue colouration.

EXAMPLE 50

The following dyeing composition is prepared:

| | |
|---|---|
| 2-Hydroxy-4-acetylaminophenoxyethanol | 1.93 g |
| Paraaminophenol | 1 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.5.

100 g of 20 volume hydrogen peroxide are added at the time of use.

When applied for 20 minutes at 30° C. to 90% naturally white hair, this mixture imparts to the hair, after rinsing and shampooing, a copper-red hue.

EXAMPLE 51

The following dyeing composition is prepared:

| | |
|---|---|
| 2-Hydroxy-4-acetylaminophenoxyethanol | 0.586 g |
| 3-Chloro-4-aminophenol hydrochloride | 0.5 g |
| 2-Butoxyethanol | 6 g |
| Hydroxyethylcellulose | 2 g |
| Ammonium lauryl-sulphate | 5 g |
| 2-Amino-2-methylpropan-1-ol | 7 g |
| Thiolactic acid | 0.4 g |
| Ethylenediaminetetraacetic acid sold under the name "TRILON B" | 0.5 g |
| Water q.s. | 100 g |

The pH of the composition is equal to 10.

60 g of 20 volume hydrogen peroxide are added at the time of use.

When applied to bleached hair for 40 minutes at 28° C., this mixture imparts to the hair, after rinsing and shampooing, a pink champagne colouration.

EXAMPLE 52

The following dyeing composition is prepared:

| | |
|---|---|
| 2-Hydroxy-4-carbethoxyaminophenoxyethanol | 0.111 g |
| Paraphenylenediamine | 0.05 g |
| Carboxymethylcellulose | 2 g |
| Ammonium lauryl-sulphate | 5 g |
| Propylene glycol | 8 g |
| 2-Butoxyethanol | 8 g |
| Pentasodium salt of diethylenetriaminepentaacetic acid, sold under the name "MASQUOL DTPA" | 2 g |
| Ammonium acetate | 1 g |
| Thioglycolic acid | 0.4 g |
| Aqueous ammonia (22° Bé) | 12 g |
| Water q.s. | 100 g |

The pH of the composition is equal to 10.5.

120 g of 20 volume hydrogen peroxide are added at the time of use.

When applied for 30 minutes at 30° C. to hair which has been bleached white, this mixture imparts to the hair, after rinsing and shampooing, a purple colouration.

EXAMPLE 53

The following dyeing composition is prepared:

| | |
|---|---|
| 1-(2'-Hydroxy-4'-acetylaminophenoxy)propane-2,3-diol | 0.066 g |
| Paraphenylenediamine | 0.03 g |
| 2-Butoxyethanol | 8 g |
| Hydroxyethylcellulose | 2 g |
| Ammonium lauryl-sulphate | 5 g |
| Thiolactic acid | 0.4 g |
| Ethylenediaminetetraacetic acid sold under the name "TRILON B" | 0.5 g |
| 2-Amino-2-methylpropan-1-ol | 3.5 g |
| Water q.s. | 100 g |

The pH of the composition is equal to 9.8.

60 g of 20 volume hydrogen peroxide are added at the time of use.

When applied for 40 minutes at 28° C. to hair which has been bleached white, this mixture imparts to the hair, after rinsing and shampooing, a tin grey colouration with purple highlights.

EXAMPLE 54

The following dyeing composition is prepared:

| | |
|---|---|
| 1-(2'-Hydroxy-4'-acetylaminophenoxy)propane-2,3-diol | 0.241 g |
| Paraphenylenediamine | 0.108 g |
| Nonylphenol ethoxylated with 4 mol of ethylene oxide, sold under the name "CEMULSOL NP$_4$" by "RHONE POULENC" | 21 g |
| Nonylphenol ethoxylated with 9 mol of ethylene oxide, sold under the name "CEMULSOL NP$_9$" by "RHONE POULENC" | 24 g |
| Oleic acid | 4 g |
| 2-Butoxyethanol | 3 g |
| Ethanol (96°) | 10 g |
| Pentasodium salt of diethylenetriaminepentaacetic acid, sold under the name "MASQUOL |  |

| | |
|---|---|
| DTPA" | 2.5 g |
| Thioglycolic acid | 0.6 g |
| Aqueous ammonia (22° Bé) | 10 g |
| Water q.s. | 100 g |

The pH of the composition is equal to 10.0.

100 g of 20 volume hydrogen peroxide are added at the time of use.

When applied for 20 minutes at 30° C. to 90% naturally white hair, this mixture imparts to the hair, after rinsing and shampooing, a grey colouration with a purple shade.

EXAMPLE 55

The following dyeing composition is prepared:

| | |
|---|---|
| 1-(2'-Hydroxy-4'-acetylaminophenoxy)propane-2,3-diol | 2.5 g |
| Paraaminophenol | 1.13 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.6.

100 g of 20 volume hydrogen peroxide are added at the time of use.

When applied for 15 minutes at 26° C. to hair which has been bleached white, this mixture imparts to the hair, after rinsing and shampooing, a mahogany colouration.

EXAMPLE 56

The following dyeing composition is prepared:

| | |
|---|---|
| 1-(2'-Hydroxy-4'-acetylaminophenoxy)propane-2,3-diol | 1.34 g |
| 3-Chloro-4-aminophenol hydrochloride | 1 g |
| Nonylphenol ethoxylated with 4 mol of ethylene oxide, sold under the name "CEMULSOL NP$_4$" by "RHONE POULENC" | 21 g |
| Nonylphenol ethoxylated with 9 mol of ethylene oxide, sold under the name "CEMULSOL NP$_9$" by "RHONE POULENC" | 24 g |
| Oleic acid | 4 g |
| 2-Butoxyethanol | 3 g |
| Ethanol (96°) | 10 g |
| Pentasodium salt of diethylenetriaminepentaacetic acid, sold under the name "MASQUOL DTPA" | 2.5 g |
| Sodium bisulphite solution (35° Bé) | 1 g |
| Aqueous ammonia (22° Bé) | 10 g |
| Water q.s. | 100 g |

The pH of the composition is equal to 10.5.

80 g of 20 volume hydrogen peroxide are added at the time of use.

When applied for 30 minutes at 27° C. to hair which has been bleached white, this mixture imparts to the hair, after rinsing and shampooing, a light copper hue.

EXAMPLE 57

The following dyeing composition is prepared:

| | |
|---|---|
| N—(2-Hydroxy-4-aminophenoxyethyl)acetamide | 0.48 g |
| Paraaminophenol | 0.25 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 9.6.

100 g of 20 volume hydrogen peroxide are added at the time of use.

When applied for 30 minutes at 28° C. to hair which has been bleached white, this mixture imparts to the hair, after rinsing and shampooing, a light copper colouration.

EXAMPLE 58

The following dyeing composition is prepared:

| | |
|---|---|
| N—(2-Hydroxy-4-aminophenoxyethyl)acetamide | 0.078 g |
| N,N—Di-β-hydroxyethylparaphenylenediamine dihydrochloride | 0.1 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.2.

100 g of 20 volume hydrogen peroxide are added at the time of use.

When applied for 30 minutes at 28° C. to hair which has been bleached white, this mixture imparts to the hair, after rinsing and shampooing, a silvery grey colouration with mauve highlights.

EXAMPLE 59

The following dyeing composition is prepared:

| | |
|---|---|
| 2-Hydroxy-4-ureidophenoxyethanol | 0.5 g |

| | |
|---|---|
| N,N—Di-β-hydroxyethylparaphenylenediamine dihydrochloride | 0.63 g |
| Cetyl/stearyl alcohol sold under the name "ALFOL C16/18 E" by "CONDEA" | 8 g |
| Sodium cetyl/stearyl-sulphate sold under the name "LANETTE WAX E" by "HENKEL" | 0.5 g |
| Ethoxylated castor oil sold under the name "CEMULSOL B" by "RHONE-POULENC" | 1 g |
| Oleic diethanolamide | 1.5 g |
| Pentasodium salt of diethylenetriaminepentaacetic acid, sold under the name "MASQUOL DTPA" | 2.5 g |
| Thioglycolic acid | 0.5 g |
| Hydroquinone | 0.4 g |
| Aqueous ammonia (22° Bé) | 10 g |
| Water q.s. | 100 g |

The pH of the composition is equal to 9.0.

100 g of 20 volume hydrogen peroxide are added at the time of use.

When applied for 30 minutes at 29° C. to hair which has been bleached white, this mixture imparts to the hair, after rinsing and shampooing, a blue colouration.

EXAMPLE 60

The following dyeing composition is prepared:

| | |
|---|---|
| N—Methyl-N—(2-hydroxy-4-aminophenoxyethyl)-acetamide | 0.46 g |
| N—Ethyl-N—carbamylmethylparaphenylenediamine | 0.5 g |
| Cetyl/stearyl alcohol sold under the name "ALFOL C16/18 E" by "CONDEA" | 8 g |
| Sodium cetyl/stearyl-sulphate sold under the name "LANETTE WAX E" by "HENKEL" | 0.5 g |
| Ethoxylated castor oil sold under the name "CEMULSOL B" by "RHONE-POULENC" | 1 g |
| Oleic diethanolamide | 1.5 g |
| Pentasodium salt of diethylenetriaminepentaacetic acid, sold under the name "MASQUOL DTPA" | 2.5 g |
| Hydroquinone | 0.5 g |
| Aqueous ammonia (22° Bé) | 10 g |
| Water q.s. | 100 g |

The pH of the composition is equal to 9.2.

100 grams of 20 volume hydrogen peroxide are added at the time of use.

When applied for 30 minutes at 30° C. to 90% naturally white hair, this mixture imparts to the hair, after rinsing and shampooing, a light chestnut colouration.

EXAMPLE 61

The following dyeing composition is prepared:

| | |
|---|---|
| 2-Hydroxy-4-N—β-hydroxyethylaminophenoxyethanol | 0.62 g |
| 2,6-Dimethylparaphenylenediamine dihydrochloride | 0.4 g |
| 2-Methyl-4-amino-5-nitrophenol | 0.42 g |
| Nonylphenol ethoxylated with 4 mol of ethylene oxide | 12 g |
| Nonylphenol ethoxylated with 9 mol of ethylene oxide | 15 g |
| Oleyl alcohol ethoxylated with 2 mol of ethylene oxide | 1.5 g |
| Oleyl alcohol ethoxylated with 4 mol of ethylene oxide | 1.5 g |
| Propylene glycol | 6 g |
| Ethylenediaminetetraacetic acid sold under the name "TRILON B" | 0.12 g |
| Mercaptosuccinic acid | 0.4 g |
| Aqueous ammonia (22° Bé) | 11 g |
| Water q.s. | 100 g |

The pH of the composition is equal to 9.5.

100 g of 20 volume hydrogen peroxide are added at the time of use.

When applied for 30 minutes at 28° C. to 90% naturally white hair, this mixture imparts to the hair, after rinsing and shampooing, a golden hazel colouration.

EXAMPLE 62

The following dyeing composition is prepared:

| | |
|---|---|
| 2-Hydroxy-4-acetylaminophenoxyethanol | 0.04 g |
| Paratoluylenediamine dihydrochloride | 1.8 g |
| N,N—Di-β-hydroxyethylparaphenylenediamine dihydrochloride | 0.5 g |
| Paraaminophenol | 0.4 g |
| Resorcinol | 0.5 g |
| Metaaminophenol | 0.2 g |
| 2,4-Diaminophenoxyethanol dihydrochloride | 0.02 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| 1-Phenyl-3-methylpyrazol-5-one | 0.15 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.0.

100 g of 20 volume hydrogen peroxide are added at the time of use.

When applied for 40 minutes at 30° C. to 90% naturally white hair, this mixture imparts to the hair, after rinsing and shampooing, a very dark brown colouration.

EXAMPLE 63

The following dyeing composition is prepared:

| | |
|---|---|
| 2-Hydroxy-4-N—ethylaminophenoxyethanol | 1.81 g |
| Paratoluylenediamine dihydrochloride | 1.80 g |
| 2-Methyl-4-amino-5-nitro-N—β-hydroxyethyl-aniline | 0.05 g |
| Nonylphenol ethoxylated with 4 mol of ethylene oxide, sold under the name "CEMULSOL NP$_4$" by "RHONE POULENC" | 21 g |
| Nonylphenol ethoxylated with 9 mol of ethylene oxide, sold under the name "CEMULSOL NP$_9$" by "RHONE POULENC" | 24 g |
| Oleic acid | 4 g |
| 2-Butoxyethanol | 3 g |
| Ethanol (96°) | 10 g |
| Pentasodium salt of diethylenetriaminepentaacetic acid, sold under the name "MASQUOL DTPA" | 2.5 g |
| Sodium bisulphite solution (35° Bé) | 1 g |
| Aqueous ammonia (22° Bé) | 10 g |
| Water q.s. | 100 g |

The pH of the composition is equal to 9.8.

100 g of 20 volume hydrogen peroxide are added at the time of use.

When applied for 20 minutes at 29° C. to hair which has been bleached white, this mixture imparts to the hair, after rinsing and shampooing, a purple-violet chestnut colouration.

EXAMPLE 64

The following dyeing composition is prepared:

| | |
|---|---|
| 2-Hydroxy-4-aminophenoxyethanol hydrate | 0.17 g |
| Paraaminophenol | 0.10 g |
| 3-Nitro-4-N'—methylamino-N,N—di-$\beta$-hydroxyethylaniline | 0.10 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.5.

100 g of 20 volume hydrogen peroxide are added at the time of use.

When applied for 30 minutes at 29° C. to hair which has been bleached white, this mixture imparts to the hair, after rinsing and shampooing, a pinkish beige colouration.

EXAMPLE 65

The following dyeing composition is prepared:

| | |
|---|---|
| 2-Hydroxy-4-acetylaminophenoxyethanol | 1 g |
| Paratoluylenediamine dihydrochloride | 1.8 g |
| Resorcinol | 0.45 g |
| Metaaminophenol | 0.2 g |
| Oleyl alcohol ethoxylated with 2 mol of ethylene oxide | 4.5 g |
| Oleyl oxide ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| 1-Phenyl-3-methylpyrazol-5-one | 0.15 g |
| Hydroquinone | 0.15 g |
| Sodium bisulphite solution (35° Be) | 1.3 g |
| Aqueous ammonia (22° Bé) | 10 g |
| Water q.s. | 100 g |

The pH of the composition is equal to 10.0.

100 g of 20 volume hydrogen peroxide are added at the time use.

When applied for 25 minutes at 30° C. to hair which has been bleached straw yellow, this mixture imparts to the hair, after rinsing and shampooing, a jet black colouration.

EXAMPLE 66

The following dyeing composition is prepared:

| | |
|---|---|
| 2-Hydroxy-4-acetylaminophenoxyethanol | 0.5 g |
| 2-Hydroxy-4-aminophenoxyethanol hydrate | 0.08 g |
| Paraphenylenediamine | 0.2 g |
| Paraaminophenol | 0.6 g |
| N,N—Di-$\beta$-hydroxyethylparaphenylenediamine dihydrochloride | 0.5 g |
| Metaaminophenol | 0.25 g |
| Resorcinol | 0.17 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.5.

100 g of 20 volume hydrogen peroxide are added at the time of use.

When applied for 25 minutes at 30° C. to hair which has been bleached white, this mixture imparts to the hair, after rinsing and shampooing, a deep purple-violet chestnut colouration.

EXAMPLE 67

The following dyeing composition is prepared:

| | |
|---|---|
| 2-Hydroxy-4-aminophenoxyethanol hydrate | 0.4 g |
| Paraaminophenol | 0.25 g |
| Paratoluylenediamine dihydrochloride | 0.21 g |
| Metaaminophenol | 0.18 g |
| Resorcinol | 0.06 g |
| 2,4-Diaminophenoxyethanol dihydrochloride | 0.085 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Thioglycolic acid | 0.5 g |
| Aqueous ammonia (22° Bé) | 10 g |
| Water q.s. | 100 g |

The pH of the composition is equal to 10.3.

100 g of 20 volume hydrogen peroxide are added at the time of use.

When applied for 30 minutes at 30° C. to 90% naturally white hair, this mixture imparts to the hair, after rinsing and shampooing, a tobacco brown colouration.

EXAMPLE 68

The following dyeing composition is prepared:

| | |
|---|---|
| 2-Hydroxy-4-aminophenoxyethanol hydrate | 0.25 g |
| Paraphenylenediamine | 0.15 g |
| Paraaminophenol | 0.3 g |
| Metaaminophenol | 0.036 g |
| 2-Methylresorcinol | 0.02 g |
| Resorcinol | 0.06 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Bé) | 1.3 g |
| Aqueous ammonia (22° Be) | 10 g |
| Water q.s. | 100 g |

The pH of the composition is equal to 10.6.

100 g of 20 volume hydrogen peroxide are added at the time of use.

When applied for 25 minutes at 28° C. to hair which has been bleached straw yellow, this mixture imparts to the hair, after rinsing and shampooing, a coppery light chestnut colouration.

EXAMPLE 69

The following dyeing composition is prepared:

| | |
|---|---|
| 1-(2'-Hydroxy-4'-aminophenoxy)propane-2,3-diol hydrochloride | 0.2 g |
| 2-Hydroxy-4-acetylaminophenoxyethanol | 0.08 g |
| Paraphenylenediamine | 0.06 g |
| Paraaminophenol | 0.3 g |
| N—Methylparaaminophenol sulphate | 0.1 g |
| Metaaminophenol | 0.15 g |
| Resorcinol | 0.1 g |
| 2,4-Diaminophenoxyethanol dihydrochloride. | 0.04 g |
| Oleyl alcohol ethoxylated with 4 mol of ethylene oxide | 4.5 g |
| Oleyl alcohol ethoxylated with 2 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| 1-Phenyl-3-methylpyrazol-5-one | 0.15 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.4.

100 g of 20 volume hydrogen peroxide are added at the time of use.

When applied for 30 minutes at 30° C. to hair which has been bleached straw yellow, this mixture imparts to the hair, after rinsing and shampooing, a mahogany colouration.

EXAMPLE 70

The following dyeing composition is prepared:

| | |
|---|---|
| 2-Hydroxy-4-aminophenoxyethanol hydrochloride monohydrate | 0.1 g |
| Paraphenylenediamine | 0.07 g |
| Paraaminophenol | 0.1 g |
| Resorcinol | 0.04 g |
| 2-Methylresorcinol | 0.04 g |
| Metaaminophenol | 0.08 g |
| 3-N—Methylamino-4-nitrophenoxyethanol | 0.04 g |
| Oleyl alcohol ethoxylated with 2 mol of ethylene oxide | 4.5 g |
| Oleyl alcohol ethoxylated with 4 mol of ethylene oxide | 4.5 g |
| Oleylamine ethoxylated with 12 mol of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96°) | 6 g |
| Pentasodium salt of diethylenetriaminepentaacetic acid, sold under the name "MASQUOL DTPA" | 2 g |
| Hydroquinone | 1.3 g |
| Sodium bisulphite solution (35° Bé) | 1.3 g |
| Aqueous ammonia (22° Bé) | 10 g |
| Water q.s. | 100 g |

The pH of the composition is equal to 10.8.

100 g of 20 volume hydrogen peroxide are added at the time of use.

When applied for 30 minutes at 30° C. to hair which has been bleached white, this mixture imparts to the hair, after rinsing and shampooing, a pinkish golden sandy colouration.

EXAMPLE 71

The following dyeing composition is prepared:

| | |
|---|---|
| Paraphenylenediamine | 0.108 g |
| N—methyl-N—[(2-hydroxy-4-acetamido)phenoxyethyl]acetamide | 0.266 g |
| Oleyl alcohol ethoxylated with 2 mol of ethylelene oxide | 4.5 g |
| Oleyl alcohol ethoxylated with 4 mol of ethylene oxide | 4.5 g |
| Oleyl amine ethoxylated with 12 mol of ethylene oxide sold under the name "ETHOMEEN TO$_{12}$" by "ARMOUR MESS" | 4.5 g |
| Diethanolamides of copra fatty acids | 9 g |
| Monopropylene glycol | 4 g |
| 2-Butoxyethanol | 8 g |
| Ethanol (96°) | 6 g |
| Pentasodium salt of diethylenetriamine pentaacetic acid sold under the name "MASQUOL DTPA" | 2 g |
| Hydroquinone | 0.15 g |
| Sodium bisulphite solution (35° Bé) | 1.3 g |
| Aqueous ammonia (22° Bé) | 10 g |
| Water q.s. | 100 g |

The pH of the composition is equal to 10.6.

100 g of 20 volume hydrogen peroxide is added at the time of use.

When applied for 25 minutes at 28° C. to hair which has been bleached white, this mixture imparts to the hair, after rinsing and shampooing, a parma pink colouration (2.5P 3/5).

We claim:

1. A metaaminophenol of the formula

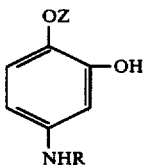

wherein Z represents a monohydroxylated or polyhydroxylated hydrocarbon radical of 1 to 6 carbon atoms and R represents hydrogen, alkyl having 1–6 carbon atoms, monohydroxyalkyl having 1–6 carbon atoms or polyhydroxyalkyl having 1–6 carbon atoms, or an acid salt thereof, with the proviso that if R represents hydrogen, Z cannot represent —CH$_2$CH$_2$OH.

2. The metaaminophenol of claim 1 wherein Z represents —CH$_2$CH$_2$OH, —CH$_2$—CHOH—CH$_2$OH or —CH$_2$—CHOH—CH$_3$.

3. The metaaminophenol of claim 1 selected from the group consisting of
2-hydroxy-4-N-ethylaminophenoxyethanol,
2-hydroxy-4-N-β-hydroxyethylaminophenoxyethanol and
1-(2-hydroxy-4-aminophenoxy)propane-2,3-diol.

4. A hair-dyeing composition comprising at least one oxidation base, a cosmetic carrier, and at least one coupler as defined in claim 1.

5. A composition according to claim 4, comprising at least one oxidation base which is:

(A) a paraphenylenediamine or paraaminophenol of formula (VI):

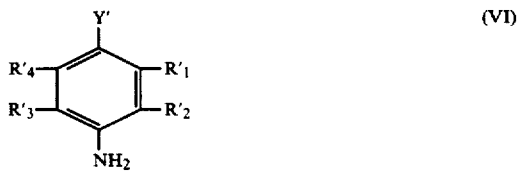

(VI)

or an acid salt thereof, wherein R'$_1$, R'$_2$, R'$_3$ and R'$_4$, which are identical or different, represent a hydrogen atom, a halogen atom or an alkyl, hydroxyalkyl, alkoxy or hydroxyalkoxy radical of 1 to 4 carbon atoms, and Y' represents a hydroxyl group or an NR'$_5$R'$_6$ group, wherein R'$_5$ and R'$_6$, which are identical or different represent a hydrogen atom or an alkyl, monohydroxyalkyl or polyhydroxyalkyl, carbamylalkyl, mesylaminoalkyl or alkoxyalkyl radical of 1 to 4 carbon atoms; or:

(B) a heterocyclic oxidation base or an acid salt thereof.

6. A composition according to claim 5, comprising at least one oxidation base which is paraphenylenediamine, paratoluylenediamine, chloroparaphenylenediamine, 2,6-dimethylparaphenylenediamine, N-β-hydroxyethylparaphenylenediamine, N-carbamylmethylparaphenylenediamine, 2,5-diaminophenoxyethanol, N,N-di-β-hydroxyethylparaphenylenediamine, N-carbamylmethyl-N-ethylparaphenylenediamine, N-methoxyethylparaphenylenediamine, 2,5-diaminophenylethanol, paraaminophenol, 2-chloro-4-aminophenol, 3-chloro-4-aminophenol, N-methylparaaminophenol, or a salt thereof, or 2,5-diaminopyridine or its acid salt.

7. A composition according to claim 4, comprising at least one complementary coupler other than those defined in claim 1, which is a metadiphenol, a metaaminophenol, a metadiamine, a heterocyclic coupler or an acid salt thereof.

8. A composition according to claim 7, wherein the complementary coupler is metaaminophenol, 2-methyl-5-aminophenol, 2-methyl-5-N-methylaminophenol, 2-methyl-5-N-β-hydroxyethylaminophenol, 2-methyl-5-N-carbamylmethylaminophenol, 2-methyl-5-N-acetylaminophenol, resorcinol, 2-methylresorcinol, 2,4-diaminophenoxyethanol, 2,4-diaminophenoxyethylamine, 1-(2',4'-diaminophenoxy)propane-2,3-diol, 2-N-β-hydroxyethylamino-4-aminoanisole, 2,6-diaminopyridine or an acid salt thereof.

9. A composition according to claim 4, comprising at least one direct dyestuff which is a nitro dyestuff of the benzene series, an anthraquinone dyestuff, or an indophenol or indoaniline.

10. A composition according to claim 9, wherein the direct dyestuff is 2-methyl-4-amino-5-nitrophenol, 3-N-methylamino-4-nitrophenoxyethanol, 2-N-β-hydroxyethylamino-5-nitroanisole, 2-amino-3-nitrophenol, 3-nitro-4-N-β-hydroxyethylaminophenol, 3-nitro-4-N'-methylamino-N,N-di-β-hydroxyethylaniline, 3-nitro-4-amino-N-β-hydroxyethylaniline, 2-methyl-4-amino-5-nitro-N-β-hydroxyethylaniline or 1,4,5,8-tetraaminoanthraquinone.

11. A composition according to claim 4, which contains from 0.01% to 4% by weight of compound according to claim 1, relative to the total weight of the composition.

12. A composition according to claim 4, wherein the cosmetic carrier comprises at least one of water, a solvent, a penetrating agent, a surface-active agent, a thickener, an antioxidant, an alkalizing or an acidifying agent, a sequestering agent, a perfume, a film-forming product or a treating agent.

13. A composition according to claim 4, which has a pH from 8 to 11.5.

14. A composition according to claim 12 which contains from 0.05 to 55% by weight of surface-active agent relative to the total weight of the composition.

15. A composition according to claim 12, which contains from 1 to 40% by weight of organic solvent relative to the total weight of the composition.

16. A composition according to claim 12, which contains from 0.5 to 5% by weight of thickener relative to the total weight of the composition.

17. A composition according to claim 12, which contains from 0.05 to 1.5% by weight of anti-oxidant relative to the total weight of the composition.

18. A composition according to claim 4, in the form of a liquid, a cream, a gel or an aerosol.

19. A hair-dyeing process, in which at the time of use, an oxidizing agent is mixed with a composition according to claim 4, the mixture is left to act on the hair for a period from 10 to 45 minutes at a temperature of from 15° to 50° C., and the hair is rinsed, optionally washed and rinsed again, and dried.

20. A process according to claim 19 wherein the oxidizing agent is hydrogen peroxide, urea peroxide or a per-salt.

* * * * *